United States Patent
Arrhenius et al.

(10) Patent No.: US 7,279,477 B2
(45) Date of Patent: Oct. 9, 2007

(54) MALONYL-COA DECARBOXYLASE INHIBITORS USEFUL AS METABOLIC MODULATORS

(75) Inventors: Thomas Arrhenius, Del Mar, CA (US); Mi Chen, San Diego, CA (US); Jie Fei Cheng, Carlsbad, CA (US); Yujin Huang, San Diego, CA (US); Alex Michael Nadzan, Encinitas, CA (US); Sovouthy Tith, San Diego, CA (US); David Mark Wallace, San Diego, CA (US); Bin Liu, Los Angeles, CA (US); Masahiro Nishimoto, Susono (JP); Gary D. Lopaschuk, Edmonton (CA); Jason R. Dyck, Sherwood Park (CA)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 194 days.

(21) Appl. No.: 10/466,926

(22) PCT Filed: Jan. 22, 2002

(86) PCT No.: PCT/US02/02179

§ 371 (c)(1),
(2), (4) Date: Jul. 21, 2003

(87) PCT Pub. No.: WO02/064136

PCT Pub. Date: Aug. 22, 2002

(65) Prior Publication Data

US 2004/0063671 A1    Apr. 1, 2004

Related U.S. Application Data

(60) Provisional application No. 60/265,380, filed on Jan. 26, 2001.

(51) Int. Cl.
*A61K 31/5375* (2006.01)
*C07D 265/30* (2006.01)

(52) U.S. Cl. .................. 514/237.8; 544/106; 544/158; 544/159; 544/160; 514/231.2; 514/237.5; 548/240; 548/300.1; 548/335.1; 548/356.1

(58) Field of Classification Search ................ 544/106, 544/158, 159, 160; 514/231.2, 237.5, 237.8; 548/240, 300.1, 335.1, 356.1
See application file for complete search history.

(56) References Cited

U.S. PATENT DOCUMENTS

| 5,177,097 A | 1/1993 | Poss |
|---|---|---|
| 5,190,942 A | 3/1993 | Poss |
| 5,208,234 A | 5/1993 | Poss |
| 5,208,235 A | 5/1993 | Poss |
| 5,212,177 A | 5/1993 | Poss |
| 5,225,408 A | 7/1993 | Weller |
| 5,256,695 A | 10/1993 | Poss |
| 5,374,615 A | 12/1994 | Poss |
| 5,378,704 A | 1/1995 | Weller |
| 5,428,033 A | 6/1995 | Belley |
| 5,470,975 A | 11/1995 | Atwal |
| 5,512,681 A | 4/1996 | Boswell |
| 5,519,143 A | 5/1996 | Harris |
| 5,534,347 A | 7/1996 | Chen |
| 5,736,297 A | 4/1998 | Roeschert |
| 5,895,771 A | 4/1999 | Epstein |
| 5,977,413 A | 11/1999 | Tomaru |
| 6,316,503 B1 * | 11/2001 | Li et al. ..................... 514/604 |

FOREIGN PATENT DOCUMENTS

| DE | 197 16 231 A1 | 10/1998 |
|---|---|---|
| DE | 197 22 952 A1 | 12/1998 |
| EP | 0 296 722 A1 | 12/1988 |
| EP | 0 481 448 A1 | 4/1992 |
| EP | 0 547 442 A1 | 6/1993 |
| EP | 0 556 060 A1 | 8/1993 |
| EP | 0 733 366 A2 | 9/1996 |
| EP | 0 733 614 A1 | 5/1998 |
| EP | 0 916 352 A2 | 12/1998 |
| FR | 2 784 114 A1 | 4/2000 |
| GB | 2 321 244 A | 7/1998 |
| GB | 2 337 701 A | 1/1999 |
| JP | 08 311036 | 11/1996 |
| JP | 09 012585 | 1/1997 |
| RU | 1743153 | 2/1995 |
| SU | 1825496 A3 | 12/1994 |
| WO | WO87/05297 | 9/1987 |
| WO | WO91/00277 | 1/1991 |
| WO | WO91/00281 | 1/1991 |
| WO | WO92/00067 | 1/1992 |
| WO | WO93/21158 | 10/1993 |
| WO | WO93/21168 | 10/1993 |
| WO | WO94/10692 | 5/1994 |
| WO | WO94/14453 | 7/1994 |
| WO | WO94/15932 | 7/1994 |
| WO | WO9418606 | 8/1994 |
| WO | WO95/35311 | 12/1995 |

(Continued)

OTHER PUBLICATIONS

Abo-Hashema, et al., Biochemistry, 1999, 15840-15847, vol. 38.

(Continued)

*Primary Examiner*—Golam M. M. Shameem
(74) *Attorney, Agent, or Firm*—Fish & Richardson P.C.

(57) ABSTRACT

The present invention relates to novel compounds (I), their prodrugs, and the pharmaceutically acceptable salts as well as pharmaceutical compositions containing such compounds useful in treating certain metabolic diseases and diseases modulated by the inhibition of the enzyme malonyl-coenzyme A decarboxylase (malonyl-CoA decarboxylase, MCD). In particular, the invention relates to compounds and compositions and the methods for the prophylaxis, management and treatment of cardiovascular diseases, diabetes, acidosis, cancers, and obesity through the inhibition of malonyl-coenzyme A decarboxylase.

14 Claims, No Drawings

FOREIGN PATENT DOCUMENTS

| | | |
|---|---|---|
| WO | WO95/35312 | 12/1995 |
| WO | WO95/35313 | 12/1995 |
| WO | WO96/13491 | 5/1996 |
| WO | WO96/13500 | 5/1996 |
| WO | WO99/12938 | 3/1999 |
| WO | WO99/47497 | 9/1999 |
| WO | WO 00/20472 | 4/2000 |
| WO | WO 00/34344 | 6/2000 |
| WO | WO 00/37422 | 6/2000 |
| WO | WO 00/46203 | 8/2000 |
| WO | WO 00/54759 | 9/2000 |
| WO | WO 00/56710 | 9/2000 |
| WO | WO 01/03705 A1 | 1/2001 |
| WO | WO 02/058690 A2 | 8/2002 |

OTHER PUBLICATIONS

Abo-Hashema, et al., Journal of Biological Chemistry, 1999, 35577-35582, Vo. 274, No. 50.
Alam and Saggerson, Bichen J., 1998, 233-241, vol. 334.
An, et al., Journal of Biochemistry and Molecular Biology, 1999, 414-418, vol. 32, No. 4.
Anderson, Current Pharmaceutical Design, 1998, 1-16, vol. 4, No. 1.
Buckner, et al., Archives of Biochemistry and Biophysics, 1976, 539-551, vol. 177.
Deems, et al., The American Physiological Society, 1998, R524-R528, vol. 274.
Dyck, et al., The American Physiological Society, 1998, H2122-H2129, vol. 275.
Farah, et al., Journal of Organic Chemistry, 1965, 998-1001, vol. 30, No. 4.
Fitzpatrick, et. al., Am. J. Hum. Genet. 1999, 318-326, vol. 65.
Fraser, et al., Febs Letters, 1999, 69-74, vol. 446.
Fujisawa, et al., TETRAHEDRON, 1998, 4267-4276, vol. 54, No. 17.
Gao, et al., Journal of Lipid Research, 1999, 178-182, vol. 40.
Hatanaka, et al., Heterocycles, 1993, 997-1004, vol. 35, No. 2.
Hearse, Metabolic Approaches to Ischaemic Heart Disease and its Management, Science Press, London, UK.
Jang, et al., The Journal of Biological Chemistry, 1989, 3500-3505, vol. 264, No. 6.
Kantor, et al., Circulation Research, 2000, 580-588, vol. 86.
Kennedy, et. al., Biochemical Pharmacology, 1996, 273-280, vol. 52.
Kim and Kolattukudy, Archives of Biochemistry and Biophysics, 1978, 585-597, vol. 190, No. 2.
Kim and Kolattukudy, Archives of Biochemistry and Biophysics, 1978, 234-246, vol. 190, No. 1.
Kim and Kolattukudy, Biochimica et Biophysica Acta, 1978, 187-196, vol. 531.
Loftus, et al., Science, 2000, 237-238, vol. 288.
McCormack, et al., Gen. Pharmac., 1998, 639-645, vol. 30, No. 5.
McGarry and Brown, Eur. J. Biochem, 1997, 1-14, vol. 244.
McNeill, Measurement of Cardiovascular Func., CRC Press, Boca Raton, USA.
Naae, J. Org. Chem., 1977, 1780-1783, vol. 42, No. 10.
Nassal, Liebigs Annalen Der Chemie, 1983, 1510-1523, No. 9.
Pepine and Wolff, The American Journal of Cardiology, 1999, 46-50, vol. 84.
Pizer, et al., Cancer Research, 2000, 213-218, vol. 60.
Prentki and Corkey, Diabetes, 1996, 273-283, vol. 45.
Randle, et al., Lancet, 1963, 785 789, vol. 1.
Sacksteder, et al., The Journal of Biological Chemistry, 1999, 24461-24468, vol. 274, No. 35.
Voilley, et al., Biochem J., 1999, 213-217, vol. 340.
Wagner, et al., Journal of The American Chemical Society, 1986, 7727-7738, vol. 108, No. 24.
Wargovich, et. al., Am J Cardiol, 1988, 65-70, vol. 61.
Zammit, Biochemical Society, 1999, 505-515, vol. 343.
Database Caplus 'Online!, Chemical Abstracts Service, XP002230054, 1999, 851-858, vol. 93, No. 8.
"Fluka Chemika-Biochemika" Fluka Chemie AG, Buchs (CH), XP002230053, 1995, 331.

\* cited by examiner

MALONYL-COA DECARBOXYLASE INHIBITORS USEFUL AS METABOLIC MODULATORS

This application claims the benefit of provisional application Ser. No. 60/265,380 filed on Jan. 26, 2001. The entire disclosure is incorporated herein by reference.

FIELD OF THE INVENTION

The present invention relates to novel compounds, their prodrugs, and the pharmaceutically acceptable salts as well as pharmaceutical compositions containing such compounds useful in treating certain metabolic diseases and diseases modulated by the inhibition of the enzyme malonyl-coenzyme A decarboxylase (malonyl-CoA decarboxylase, MCD). In particular, the invention relates to compounds and compositions and the methods for the prophylaxis, management and treatment of cardiovascular diseases, diabetes, acidosis, cancers, and obesity through the inhibition of malonyl-coenzyme A decarboxylase.

BACKGROUND

Malonyl-CoA is an important metabolic intermediary produced by the enzyme Acetyl CoA Carboxylase (ACC) in the body. In the liver, adipocytes, and other tissues, malonyl-CoA is a substrate for fatty acid synthase (FAS). ACC and malonyl-CoA are found in skeletal muscle and cardiac muscle tissue, where fatty acid synthase levels are low. The enzyme malonyl-CoA decarboxylase (MCD, EC 4.1.1.9) catalyzes the conversion of malonyl-CoA to acetyl-CoA and thereby regulates malonyl-CoA levels. MCD activity has been described in a wide array of organisms, including prokaryotes, birds, and mammals. It has been purified from the bacteria *Rhizobium trifolii* (An et al., *J. Biochem. Mol. Biol.* 32:414-418(1999)), the uropygial glands of waterfowl (Buckner, et al., *Arch. Biochem. Biophys* 177:539(1976); Kim and Kolattukudy *Arch. Biochem. Biophys* 190:585 (1978)), rat liver mitochondria (Kim and Kolattukudy, *Arch. Biochem. Biophys.* 190:234(1978)), rat mammary glands (Kim and Kolattukudy, *Biochim. Biophys, Acta* 531:187 (1978)), rat pancreatic β-cell (Voilley et al., *Biochem. J.* 340:213 (1999)) and goose (Anser anser) (Jang et al., *J. Biol. Chem.* 264:3500 (1989)). Identification of patients with MCD deficiency lead to the cloning of a human gene homologous to goose and rat MCD genes (Gao et al., *J. Lipid. Res.* 40:178 (1999); Sacksteder et al., *J. Biol. Chem.* 274:24461(1999); FitzPatrick et al., *Am. J. Hum. Genet.* 65:318(1999)). A single human MCD mRNA is observed by Northern Blot analysis. The highest mRNA expression levels are found in muscle and heart tissues, followed by liver, kidney and pancreas, with detectable amounts in all other tissues examined.

Malonyl-CoA is a potent endogenous inhibitor of carnitine palmitoyltransferase-I (CPT-I), an enzyme essential for the metabolism of long-chain fatty acids. CPT-I is the rate-limiting enzyme in fatty acid oxidation and catalyzes the formation of acyl-carnitine, which is transported from the cytosol across the mitochondrial membranes by acyl carnitine translocase. Inside of the mitochondria the long-chain fatty acids are transferred back to CoA form by a complementary enzyme, CPT-II, and, in the mitochondria, acyl-CoA enters the β-oxidation pathway generating acetyl-CoA. In the liver, high levels of acetyl-CoA occurs for example following a meal, leading to elevated malonyl-CoA levels, which inhibit CPT-I, thereby preventing fat metabolism and favoring fat synthesis. Conversely, low malonyl-CoA levels favor fatty acid metabolism by allowing the transport of long-chain fatty acids into the mitochondria. Hence, malonyl-CoA is a central metabolite that plays a key role in balancing fatty acid synthesis and fatty acid oxidation (Zammit, *Biochem. J.* 343:5050-515(1999)). Recent work indicates that MCD is able to regulate cytoplasmic as well as mitochondrial malonyl-CoA levels [Alam and Saggerson, *Biochem J.* 334:233-241(1998); Dyck et al., *Am J Physiology* 275:H2122-2129(1998)].

Although malonyl-CoA is present in muscle and cardiac tissues, only low levels of FAS have been detected in these tissues. It is believed that the role of malonyl-CoA and MCD in these tissues is to regulate fatty acid metabolism. This is achieved via malonyl-CoA inhibition of muscle (M) and liver (L) isoforms of CPT-I, which are encoded by distinct genes (McGarry and Brown, *Eur. J. Biochem.* 244:1-14 (1997)). The muscle isoform is more sensitive to malonyl-CoA inhibition ($IC_{50}$ 0.03 μM) than the liver isoform ($IC_{50}$ 2.5 μM). Malonyl-CoA regulation of CPT-I has been described in the liver, heart, skeletal muscle and pancreatic β-cells. In addition, malonyl-CoA sensitive acyl-CoA transferase activity present in microsomes, perhaps part of a system that delivers acyl groups into the endoplasmic reticulum, has also been described (Fraser et al., *FEBS Lett.* 446: 69-74 (1999)).

Cardiovascular Diseases: The healthy human heart utilizes available metabolic substrates. When blood glucose levels are high, uptake and metabolism of glucose provide the major source of fuel for the heart. In the fasting state, lipids are provided by adipose tissues, and fatty acid uptake and metabolism in the heart down regulate glucose metabolism. The regulation of intermediary metabolism by serum levels of fatty acid and glucose comprises the glucose-fatty acid cycle (Randle et al., *Lancet*, 1:785-789(1963)). Under ischemic conditions, limited oxygen supply reduces both fatty acid and glucose oxidation and reduces the amount of ATP produced by oxidative phosphorylation in the cardiac tissues. In the absence of sufficient oxygen, glycolysis increases in an attempt to maintain ATP levels and a buildup of lactate and a drop in intracellular pH results. Energy is spent maintaining ion homeostasis, and myocyte cell death occurs as a result of abnormally low ATP levels and disrupted cellular osmolarity. Additionally, AMPK, activated during ischemia, phosphorylates and thus inactivates ACC. Total cardiac malonyl-CoA levels drop, CPT-I activity therefore is increased and fatty acid oxidation is favored over glucose oxidation. The beneficial effects of metabolic modulators in cardiac tissue are the increased efficiency of ATP/mole oxygen for glucose as compared to fatty acids and more importantly the increased coupling of glycolysis to glucose oxidation resulting in the net reduction of the proton burden in the ischemic tissue.

A number of clinical and experimental studies indicate that shifting energy metabolism in the heart towards glucose oxidation is an effective approach to decreasing the symptoms associated with cardiovascular diseases, such as but not limited, to myocardial ischemia (Hearse, "*Metabolic approaches to ischemic heart disease and its management*", Science Press). Several clinically proven anti-angina drugs including perhexiline and amiodarone inhibit fatty acid oxidation via inhibition of CPT-I (Kennedy et al., *Biochem. Pharmacology*, 52: 273 (1996)). The antianginal drugs ranolazine, currently in Phase III clinical trials, and trimetazidine are shown to inhibit fatty acid β-oxidation (McCormack et al., *Genet. Pharmac.* 30:639(1998), Pepine et al., *Am. J. Cardiology* 84:46 (1999)). Trimetazidine has been shown to specifically inhibit the long-chain 3-ketoactyl CoA thiolase, an essential step in fatty acid oxidation. (Kantor et al., *Circ. Res.* 86:580-588 (2000)). Dichloroacetate increases glucose oxidation by stimulating the pyruvate dehydrogenase complex and improves cardiac function in those patients with coronary artery diseases (Wargovich et al., *Am. J. Cardiol.* 61:65-70 (1996)). Inhibiting CPT-I activity through the increased malonyl-CoA levels with MCD inhibitors would result in not only a novel, but also a much safer method, as compared to other known small molecule CPT-I inhibitors, to the prophylaxis and treatment of cardiovascular diseases.

Most of the steps involved in glycerol-lipid synthesis occur on the cytosolic side of liver endoplasmic reticulum (ER) membrane. The synthesis of triacyl glycerol (TAG) targeted for secretion inside the ER from diacyl gycerol (DAG) and acyl CoA is dependent upon acyl CoA transport across the ER membrane. This transport is dependent upon a malonyl-CoA sensitive acyl-CoA transferase activity (Zammit, *Biochem. J.* 343: 505(1999) Abo-Hashema, *Biochem.* 38: 15840 (1999) and Abo-Hashema, *J. Biol. Chem.* 274:35577 (1999)). Inhibition of TAG biosynthesis by a MCD inhibitor may improve the blood lipid profile and therefore reduce the risk factor for coronary artery disease of patients.

Diabetes: Two metabolic complications most commonly associated with diabetes are hepatic overproduction of ketone bodies (in NIDDM) and organ toxicity associated with sustained elevated levels of glucose. Inhibition of fatty acid oxidation can regulate blood-glucose levels and ameliorate some symptoms of type II diabetes. Malonyl-CoA inhibition of CPT-I is the most important regulatory mechanism that controls the rate of fatty acid oxidation during the onset of the hypoinsulinemic-hyperglucagonemic state. Several irreversible and reversible CPT-I inhibitors have been evaluated for their ability to control blood glucose levels and they are all invariably hypoglycemic (Anderson, *Current Pharmaceutical Design* 4:1(1998)). A liver specific and reversible CPT-inhibitor, SDZ-CPI-975, significantly lowers glucose levels in normal 18-hour-fasted nonhuman primates and rats without inducing cardiac hypertrophy (Deems et al., *Am. J. Physiology* 274:R524 (1998)). Malonyl-CoA plays a significant role as a sensor of the relative availability of glucose and fatty acid in pancreatic β-cells, and thus links glucose metabolism to cellular energy status and insulin secretion. It has been shown that insulin secretagogues elevate malonyl-CoA concentration in β-cells (Prentki et al., *Diabetes* 45: 273 (1996)). Treating diabetes directly with CPT-I inhibitors has, however, resulted in mechanism-based hepatic and myocardial toxicities. MCD inhibitors that inhibit CPT-I through the increase of its endogenous inhibitor, malonyl-CoA, are thus safer and superior as compared to CPT-I inhibitors for treatment of diabetic diseases.

Cancers: Malonyl-CoA has been suggested to be a potential mediator of cytotoxicity induced by fatty-acid synthase inhibition in human breast cancer cells and xenografts (Pizer et al., *Cancer Res.* 60:213 (2000)). It is found that inhibition of fatty acid synthase using antitumor antibiotic cerulenin or a synthetic analog C75 markedly increase the malonyl-CoA levels in breast carcinoma cells. On the other hand, the fatty acid synthesis inhibitor, TOFA (5-(tetradecyloxy)-2-furoic acid), which only inhibits at the acetyl-CoA carboxylase (ACC) level, does not show any antitumor activity, while at the same time the malonyl-CoA level is decreased to 60% of the control. It is believed that the increased malonyl-CoA level is responsible for the antitumor activity of these fatty acid synthase inhibitors. Regulating malonyl-CoA levels using MCD inhibitors thus constitutes a valuable therapeutic strategy for the treatment of cancer diseases.

Obesity: It is suggested that malonyl-CoA may play a key role in appetite signaling in the brain via the inhibition of the neuropepetide Y pathway (Loftus et al., *Science* 288: 2379 (2000)). Systemic or intracerebroventricular treatment of mice with fatty acid synthase (FAS) inhibitor cerulenin or C75 led to inhibition of feeding and dramatic weight loss. It is found that C75 inhibited expression of the prophagic signal neuropeptide Y in the hypothalamus and acted in a leptin-independent manner that appears to be mediated by malonyl-CoA. Therefore control of malonyl-CoA levels through inhibition of MCD provides a novel approach to the prophylaxis and treatment of obesity.

The design of MCD inhibitors for the treatment of cardiovascular diseases, diabetes, cancers or obesity has not been reported in the literature. We have now found a novel series of compounds containing hexafluoroisopropanol or trifluoromethyl ketone or similar moieties, members of which are potent inhibitors of MCD. The compounds tested both in vitro and in vivo inhibit malonyl-CoA decarboxylase activities and increase the malonyl-CoA concentration in the body. In addition, by way of example, selected compounds induce a significant increase in glucose oxidation as compared with the control in an isolated perfused rat heart assay (McNeill, *Measurement of Cardiovascular Function*, CRC Press, 1997).

Advantageously, preferred compounds, such as Compounds 1a of the invention, have more profound effects in metabolism shift than the known metabolism modulators such as ranolazine or trimetazidine. The compounds of the invention and pharmaceutical composition containing these compounds are therefore useful in medicine, especially in the prophylaxis, management and treatment of various cardiovascular diseases, diabetes, cancers and obesity.

Additionally, these compounds are also useful as a diagnostic tool for diseases associated with MCD deficiency or malfunctions.

SUMMARY OF THE INVENTION

The present invention provides novel compounds as depicted in Formula (I), novel pharmaceutical compositions containing the same and methods for the prophylaxis, management and treatment of metabolic diseases and diseases modulated by MCD inhibition. The compounds of this invention are useful for the prophylaxis, management and treatment of diseases involving in malonyl-CoA regulated glucose/fatty acid metabolism pathways. In particular, these compounds and pharmaceutical compositions containing the same are indicated in the prophylaxis, management and treatment of cardiovascular diseases, diabetes, cancers and obesity. In addition to the novel compounds and compositions of this invention, the intermediates and processes useful for the preparation of the compounds of the invention are also included within the scope of this invention.

The present invention also includes within its scope diagnostic methods for the detection of diseases associated with MCD deficiency or malfunctions.

The compounds of the invention are represented by the following general structure (I):

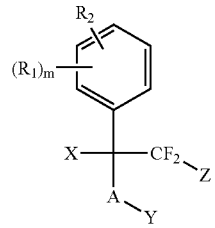

their prodrugs and pharmaceutically acceptable salts, wherein $R_1$, $R_2$, A, m, X, Y, and Z are as defined below. Other aspects of this invention will become apparent as the description of this invention continues. Hence, the foregoing merely summarizes certain aspects of the invention and is not intended, nor should it be construed, as limiting the invention in any way.

DETAILED DESCRIPTION OF THE INVENTION

The detailed description of the invention that follows is not intended to be exhaustive or to limit the invention to the precise details disclosed. It has been chosen and described to best explain the details of the invention to others skilled in the art.

The compounds of the invention are represented by the following general structure (I):

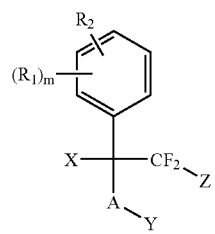

wherein $R_1$ is independently chosen from halo, haloalkyl, hydroxy, thiol, substituted thiol, sulfonyl, sulfinyl, nitro, cyano, amino, substituted amino, $C_1$-$C_6$ alkyl and $C_1$-$C_6$ alkoxy, and when $R_1$ is hydroxy, $C_1$-$C_6$ alkoxy, thiol, substituted thiol, amino, substituted amino, or $C_1$-$C_6$ alkyl, such radical may be combined with $R_2$ to form a ring of 5-7 members when $R_1$ is ortho to $R_2$;

$R_2$ is selected from $NR_3C(S)NR_4R_5$, $NR_3C(=NR_3)NR_4R_5$, $NR_3C(=NCN)NR_4R_5$, $NR_3C(=CHNO_2)NR_4R_5$, $NR_3P(O)R_4R_5$, $NR_3P(O)(OR_4)(OR_5)$, $NR_3P(O)(OR_4)(NR_5)$, $NR_3P(O)(NR_4)(NR_5)$, $NR_3C(=NR_3)R_6$, $COR_6$, $R_6C(OH)R_7$, $CR_8=NOR_4$, $CR_8=NR_3$, $CR_8=NNR_4R_5$, $SOR_7$, $SO_2R_7$, $P(O)(OR_4)(OR_5)$, $P(O)(R_4)(R_5)$, $P(O)(OR_4)(OR_5)$, $P(O)(NR_3)(OR_4)$, $P(O)(NR_4)(NR_5)$, a 3-7 membered ring containing from zero to three heteroatoms selected from O, N, or S, which may be substituted by $R_9$, $R_{10}$, $R_{11}$, $R_{12}$ or $R_{13}$, with the exception of the following groups:

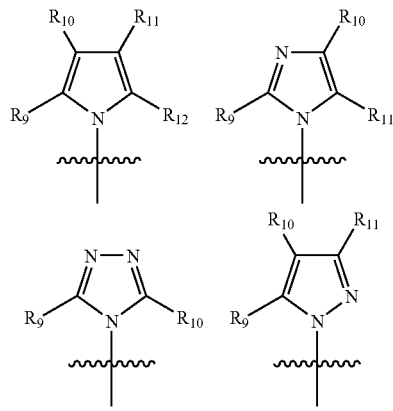

or may be combined with $R_1$ to form a ring of 5-7 members when $R_1$ is ortho to $R_2$;

$R_3$ is hydrogen, alkyl, aryl, heterocyclyl, acyl, or may form a ring of 5-7 members with $R_4$ or $R_5$;

$R_4$ is hydrogen, alkyl, aryl, heterocyclyl, acyl, or may form a ring of 5-7 members with $R_5$ or $R_3$;

$R_5$ is hydrogen, alkyl, aryl, or heterocyclyl, acyl or may form a ring of 5-7 members with $R_3$ or $R_4$;

$R_6$ and $R_7$ may be equal or different and are selected from hydrogen, alkyl, aryl, or heterocylcyl;

$R_8$ is hydrogen, alkyl, aryl, heterocylcyl, amino or substituted amino;

$R_9$, $R_{10}$, $R_{11}$ and $R_{12}$ may be equal or different and are selected from hydrogen, alkyl, aryl, heterocyclyl, nitro, cyano, carboxylic acid, ester, amide, halo, hydroxyl, amino, substituted amino, alkoxy, acyl, ureido, sulfonamido, sulfamido, sulfonyl, sulfinyl, or guanadinyl;

$R_{13}$ is hydrogen, alkyl, aryl, heterocyclyl, acyl, ester, sulfonyl, ureido, or guanadinyl;

A is O, S, or $NR_3$;

m is from zero to four;

X is H, $CF_2Z$, or $CF_3$, or together with Y forms a double bond when A is O;

Y is hydrogen, or together with X forms a double bond when A is O;

Z is F, Br, Cl, I or $CF_3$;

their prodrugs and pharmaceutically acceptable salts. The enantiomers, diasteromers, or tautomers of the compound (I) are also encompassed in the present invention.

Preferably, the compounds of this invention have the following general structures (Ia and Ib):

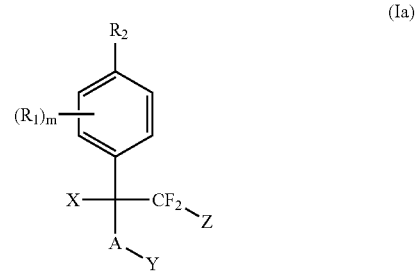

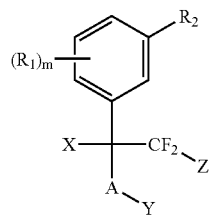

(Ib)

wherein $R_1$, $R_2$, A, m, X, Y, and Z are as defined above.

More preferred compounds are depicted in the following general structures (Ic and Id):

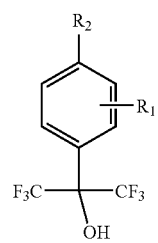

(Ic)

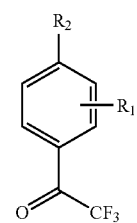

(Id)

wherein $R_2$ is as defined above and $R_1$ is hydrogen, halo, hydroxyl, or cyano group.

Still more preferred embodiment relates to compounds Ic and Id wherein $R_2$ is selected from the following groups:

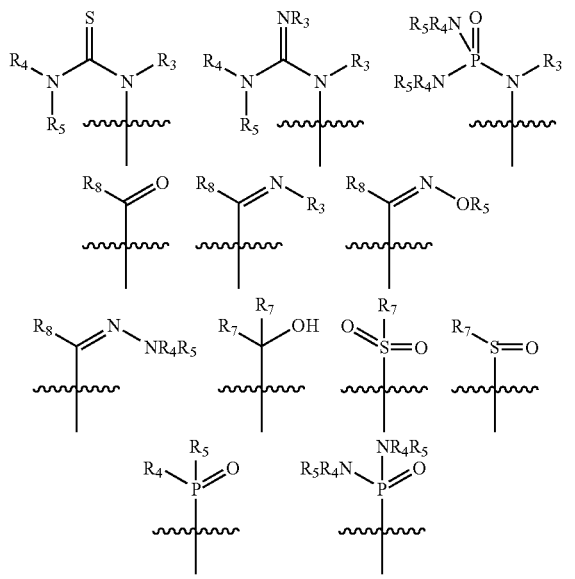

wherein $R_3$, $R_4$, $R_5$, $R_6$, $R_7$, and $R_8$ are as defined as above.

Still more preferred embodiment relates to compounds Ic and Id wherein $R_2$ is a five membered heterocyclic ring containing two to three heteroatoms. Five membered heterocyclic rings include imidazole/imidazoline pyrazole/pyrazoline, thiazole, oxazole, isoxazole, isoxazoline, triazole, thiazolidone, imidazolidone as exemplified as follows:

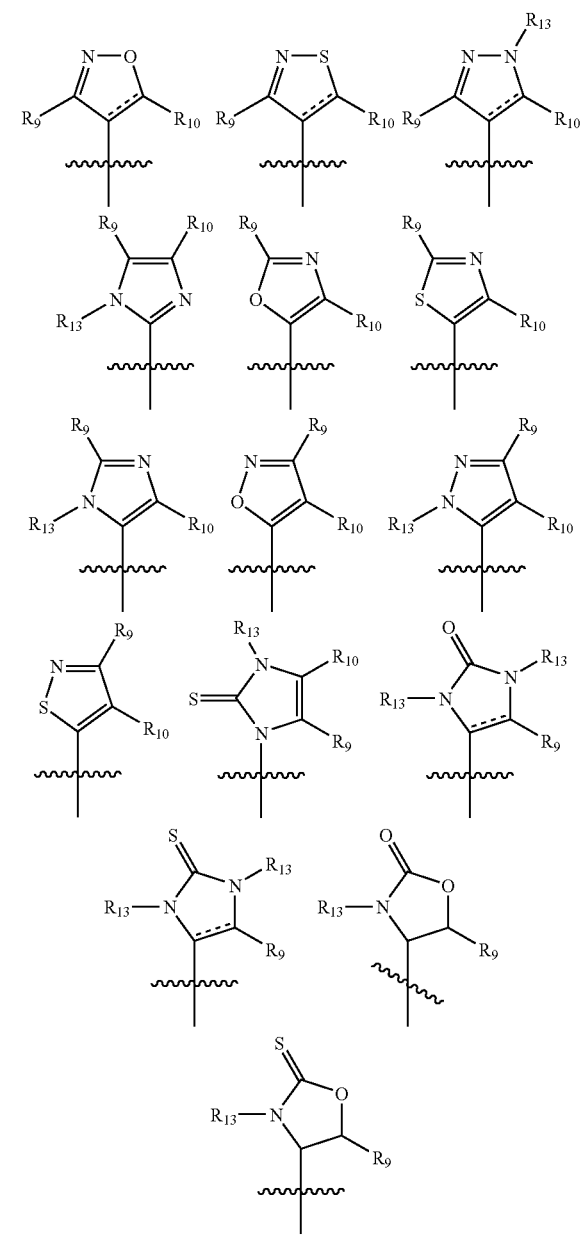

wherein $R_9$, $R_{10}$, and $R_{13}$ are defined as above.

Definitions

As used herein, "alkyl" means a cyclic, branched, or straight chain chemical group containing only carbon and hydrogen, such as methyl, pentyl, and adamantyl. Alkyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Alkyl groups can be saturated or unsaturated (e.g., containing —C=C— or —C≡C— subunits), at one or several positions. Typically, alkyl groups will comprise 1 to 12 carbon atoms, preferably 1 to 10, and more preferably 1 to 8 carbon atoms or cyclic groups containing three to eight carbons.

As used herein, "lower alkyl" means a subset of alkyl, and thus is a hydrocarbon substituent, which is linear, cyclic or branched. Preferred lower alkyls are of 1 to about 6 carbons, and may be branched or linear, and may include cyclic substituents, either as part or all of their structure. Examples of lower alkyl include butyl, propyl, isopropyl, ethyl, and methyl. Likewise, radicals using the terminology "lower" refer to radicals preferably with 1 to about 6 carbons in the alkyl portion of the radical.

As used herein, "amido" means a H—CON— or alkyl-CON—, aryl-CON— or heterocyclyl-CON group wherein the alkyl, aryl or heterocyclyl group is as herein described.

As used herein, "aryl" means a substituted or unsubstituted aromatic radical having a single-ring (e.g., phenyl) or multiple condensed rings (e.g., naphthyl or anthryl), which can be optionally unsubstituted or substituted with amino, cyano, hydroxyl, lower alkyl, haloalkyl, alkoxy, nitro, halo, mercapto, and other substituents, and which may or may not include one or more heteroatoms. Preferred carbocyclic aryl is phenyl. The term "heteroaryl" is clearly contemplated in the term "aryl". Preferably where the term aryl represents a heterocycle, it is referred to as "heteroaryl", and has one or more heteroatom(s). Preferred are monocyclic heterocycles of 5 or 6 members. Hence preferred heteroaryl is a monovalent unsaturated aromatic group having a single ring and having at least one hetero atom, such as N, O, or S, within the ring, which can optionally be unsubstituted or substituted with amino, cyano, nitro, hydroxyl, alkyl, haloalkyl, alkoxy, aryl, halo, mercapto, oxo (hence forming a carbonyl,) and other substituents. Examples of heteroaryl include thienyl, pyrridyl, furyl, oxazolyl, oxadiazolyl, pyrollyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl and others.

In this definition it is clearly contemplated that substitution on the aryl ring is within the scope of this invention. Where substitution occurs, the radical is called substituted aryl. Preferably one to three, more preferably one or two, and most preferably one substituent occur on the aryl ring. Preferred substitution patterns in five membered rings are substituted in the 2 position relative to the connection to the claimed molecule. Though many substituents will be useful, preferred substituents include those commonly found in aryl compounds, such as alkyl, hydroxy, alkoxy, cyano, nitro, halo, haloalkyl, mercapto and the like.

As used herein, "amide" includes both RNR'CO— (in the case of R=alkyl, alkaminocarbonyl-) and RCONR'— (in the case of R=alkyl, alkyl carbonylamino-).

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO— or alkyl-CO—, aryl-CO— or heterocyclyl-CO— group wherein the alkyl, aryl or heterocyclyl group is as herein described. Preferred acyls contain a lower alkyl. Exemplary alkyl acyl groups include formyl, acetyl, propanoyl, 2-methylpropanoyl, t-butylacetyl, butanoyl and palmitoyl.

As used herein, "halo" is a chloro, bromo, fluoro or iodo atom radical. Chloro, bromo and fluoro are preferred halides. The term "halo" also contemplates terms sometimes referred to as "halogen", or "halide".

As used herein, "haloalkyl" means a hydrocarbon substituent, which is linear or branched or cyclic alkyl, alkenyl or alkynyl substituted with chloro, bromo, fluoro or iodo atom(s). Most preferred of these are fluoroalkyls, wherein one or more of the hydrogen atoms have been substituted by fluoro. Preferred haloalkyls are of 1 to about 5 carbons in length, More preferred haloalkyls are 1 to about 4 carbons, and most preferred are 1 to 3 carbons in length. The skilled artisan will recognize then that as used herein, "haloalkylene" means a diradical variant of haloalkyl, such diradicals may act as spacers between radicals, other atoms, or between the parent ring and another functional group. For example, the linker. CHF—CHF is a haloakylene diradical.

As used herein, "heterocyclyl" means heterocyclic radicals, which are saturated or unsaturated. These may be substituted or unsubstituted, and are attached to other via any available valence, preferably any available carbon or nitrogen. More preferred heterocycles are of 5 or 6 members. In six membered non-aromatic monocyclic heterocycles, the heteroatom(s) are selected from one up to three of O, N or S, and wherein when the heterocycle is five membered and non-aromatic, preferably it has one or two heteroatoms selected from O, N, or S.

As used herein, "substituted amino" means an amino radical which is substituted by one or two alkyl, aryl, or heterocyclyl groups, wherein the alkyl, aryl or heterocyclyl are defined as above.

As used herein, "substituted thiol" means RS— group wherein R is an alkyl, an aryl, or a heterocyclyl group, wherein the alkyl, aryl or heterocyclyl are defined as above.

As used herein, "sulfonyl" means an alkylSO$_2$, arylSO$_2$ or heterocyclyl-SO$_2$ group wherein the alkyl, aryl or heterocyclyl are defined as above.

As used herein, "sulfamido" means an alkyl-N—S(O)$_2$N—, aryl-NS(O)$_2$N— or heterocyclyl-NS(O)$_2$N— group wherein the alkyl, aryl or heterocylcyl group is as herein described.

As used herein, "sulfonamido" means an alkyl-S(O)$_2$N—, aryl-S(O)$_2$N— or heterocyclyl-S(O)$_2$N— group wherein the alkyl, aryl or heterocyclyl group is as herein described.

As used herein, "ureido" means an alkyl-NCON—, aryl-NCON— or heterocyclyl-NCON— group wherein the alkyl, aryl or heterocyclyl group is as herein described A used herein, a "radical" may form a ring with another radical as described herein. When such radicals are combined, the skilled artisan will understand that there are no unsatisfied valences in such a case, but that specific substitutions, for example a bond for a hydrogen, is made. Hence certain radicals can be described as forming rings together. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members. As used herein the term "ring" or "rings" when formed by the combination of two radicals refers to heterocyclic or carbocyclic radicals, and such radicals may be saturated, unsaturated, or aromatic. For example, preferred heterocyclic ring systems include heterocyclic rings, such as morpholinyl, piperdinyl, imidazolyl, pyrrolidinyl, and pyridinyl.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this invention, though such resonance forms or tautomers are not represented herein. For example,

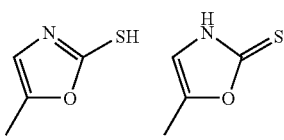

the above substructures clearly represent the same radical and reference to either clearly contemplates the other. In addition, the following compounds may represent prodrugs when R can be removed by biological processes in situ:

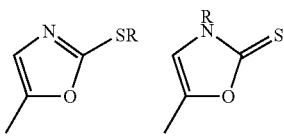

Compounds and compositions herein also specifically contemplate pharmaceutically acceptable salts, whether cationic or anionic. A "pharmaceutically-acceptable salt" is an anionic salt formed at any acidic (e.g., carboxyl) group, or a cationic salt formed at any basic (e.g., amino) group. Many such salts are known in the art, as described in World Patent Publication 87/05297, Johnston et al., published Sep. 11, 1987 (incorporated by reference herein). Preferred counterions of salts formable at acidic groups can include cations of salts, such as the alkali metal salts (such as sodium and potassium), and alkaline earth metal salts (such as magnesium and calcium) and organic salts. Preferred salts formable at basic sites include anions such as the halides (such as chloride salts). Of course, the skilled artisan is aware that a great number and variation of salts may be used, and examples exist in the literature of either organic or inorganic salts useful in this manner.

It is also clearly contemplated that compounds of the invention can be provided as biohydrolyzable prodrugs, as they are understood in the art. "Prodrug", as used herein is any compound wherein when it is exposed to the biological processes in an organism, is hydrolyzed, metabolized, derivatized or the like, to yield an active substance having the desired activity. The skilled artisan will recognize that prodrugs may or may not have any activity as prodrugs. It is the intent that the prodrugs described herein have no deleterious effect on the subject to be treated when dosed in safe and effective amounts. These include for example, biohydrolyzable amides and esters. A "biohydrolyzable amide" is an amide compound which does not essentially interfere with the activity of the compound, or that is readily converted in vivo by a cell, tissue, or human, mammal, or animal subject to yield an active compound of the invention. A "biohydrolyzable ester" refers to an ester compound of the invention that does not interfere with the activity of these compounds or that is readily converted by an animal to yield an active formula (I) compound. Such biohydrolyzable prodrugs are understood by the skilled artisan and are embodied in regulatory guidelines.

Inasmuch as the compounds of the invention may contain optical centers, "optical isomer", "stereoisomer", "enantiomer," "diastereomer," as referred to herein have the standard art recognized meanings (cf. *Hawleys Condensed Chemical Dictionary*, 11th Ed.) and are included in the compounds claimed, whether as racemates, or their optical isomers, stereoisomers, enantiomers, diastereomers.

As used herein "cardiovascular diseases" include arrhthymia, atrial fibrillation, congestive heart failure, coronary artery disease, hypertension, myocardial infarction, stroke, ventricular fibrillation, among others, particularly cardiovascular ischemia such as angina pectoris and those conditions treatable by shifting metabolism within the cardiovascular system.

As used herein, the term "metabolic disease", means disorders in a mammal in which errors of metabolism, imbalances in metabolism, or sub-optimal metabolism occur. The metabolic diseases as used herein also contemplate a disease that can be treated through the modulation of metabolism, although the disease itself may or may not be caused by specific metabolism blockage. Particularly, such metabolic disease involves glucose and fatty acid oxidation pathway. Still more particularly, such metabolic disease involves MCD or is modulated by levels of Malonyl-CoA. All these conditions are collectively referred to herein as an "MCD or MCA related disorder."

Compositions

The compositions of the present invention comprise:
(a) a safe and therapeutically effective amount of an MCD inhibiting compound (I), prodrug or pharmaceutical salt thereof; and
(b) a pharmaceutically-acceptable carrier.

As discussed above, numerous diseases can be mediated by MCD related therapy. Thus, the compounds of this invention are useful in therapy with regard to conditions involving this MCD activity.

Accordingly, the compounds of this invention can therefore be formulated into pharmaceutical compositions for use in prophylaxis, management and treatment of these conditions. Standard pharmaceutical formulation techniques are used, such as those disclosed in Remington's Pharmaceutical Sciences, Mack Publishing Company, Easton, Pa.

A "safe and therapeutically effective amount" of a compound of the present invention is an amount that is effective, to inhibit MCD at the site(s) of activity, in a subject, a tissue, or a cell, and preferably in an animal, more preferably in a mammal, without undue adverse side effects (such as toxicity, irritation, or allergic response), commensurate with a reasonable benefit/risk ratio, when used in the manner of this invention. The specific "safe and therapeutically effective amount" will, obviously, vary with such factors as the particular condition being treated, the physical condition of the patient, the duration of treatment, the nature of concurrent therapy (if any), the specific dosage form to be used, the carrier employed, the solubility of the compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4. In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a compound that is suitable for administration to an animal, preferably mammal subject, in a single dose, according to good medical practice. (The preparation of a single or unit dosage form however, does not imply that the dosage form is administered once per day or once per course of therapy. Such dosage forms are contemplated to be administered once, twice, thrice or more per day, and are expected to be given more than once during a course of therapy, though a single administration is not specifically excluded. The skilled artisan will recognize that the formulation does not specifically contemplate the entire course of therapy and such decisions are left for those skilled in the art of treatment rather than formulation.) These compositions preferably contain from about 5 mg (milligrams), more preferably from about 10 mg to about 1000 mg, more preferably to about 500 mg, most preferably to about 300 mg, of the selected compound.

The compositions of this invention may be in any of a variety of forms, suitable (for example) for oral, nasal, rectal, topical (including transdermal), ocular, intracereberally, intravenous, intramuscular, or parenteral administration. (The skilled artisan will appreciate that oral and nasal compositions comprise compositions that are administered by inhalation, and made using available methodologies.) Depending upon the particular route of administration desired, a variety of pharmaceutically-acceptable carriers well-known in the art may be used. These include solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods of this invention are described in the following references, all incorporated by reference herein: Modern Pharmaceutics, Chapters 9 and 10 (Banker & Rhodes, editors, 1979); Lieberman et al., Pharmaceutical Dosage Forms: Tablets (1981); and Ansel, Introduction to Pharmaceutical Dosage Forms 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct application or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the compound. Suitable carriers for topical administration preferably remain in place on the skin as a continuous film, and resist being removed by perspiration or immersion in water. Generally, the carrier is organic in nature and capable of having dispersed or dissolved therein the compound. The carrier may include pharmaceutically-acceptable emollient, emulsifiers, thickening agents, solvents and the like.

Methods of Administration

The compounds and compositions of this invention can be administered topically or systemically. Systemic application includes any method of introducing compound into the tissues of the body, e.g., intra-articular, intrathecal, epidural., intramuscular, transdermal, intravenous, intraperitoneal, subcutaneous, sublingual administration, inhalation, rectal, or oral administration. The compounds of the present invention are preferably administered orally.

The specific dosage of the compound to be administered, as well as the duration of treatment is to be individualised by the treating clinicians. Typically, for a human adult (weighing approximately 70 kilograms), from about 5 mg, preferably from about 10 mg to about 3000 mg, more preferably to about 1000 mg, more preferably to about 300 mg, of the selected compound is administered per day. It is understood that these dosage ranges are by way of example only, and that daily administration can be adjusted depending on the factors listed above.

In all of the foregoing, of course, the compounds of the invention can be administered alone or as mixtures, and the compositions may further include additional drugs or excipients as appropriate for the indication. For example, in the treatment of cardiovascular diseases, it is clearly contemplated that the invention may be used in conjunction with beta-blockers, calcium antagonists, ACE inhibitors, diuretics, angiotensin receptor inhibitors, or known cardiovascular drugs or therapies. Hence, in this example, novel compounds or compositions of this invention are useful when dosed together with another active and can be combined in a single dosage form or composition.

The compositions can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Preparation of Compounds of the Invention

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the claimed compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March *Advanced Organic Chemistry* (Wiley), Carey and Sundberg, *Advanced Organic Chemistry* and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protecting Groups in Organic Synthesis*, $2^{nd}$ Ed., John Wiley & Sons (1991).

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure.

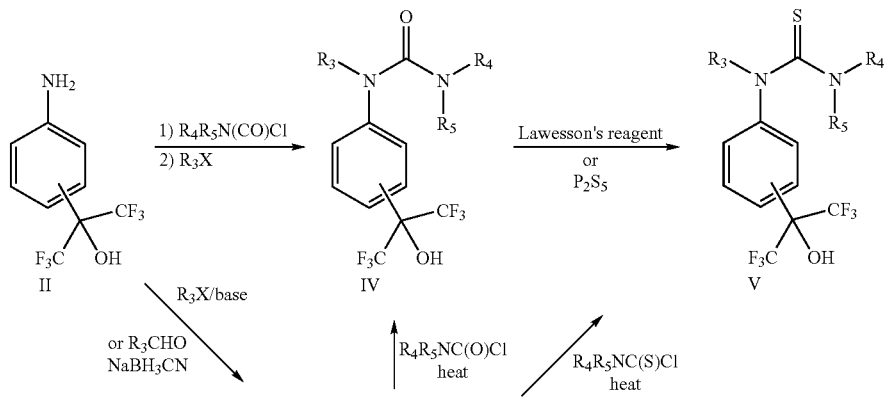

Scheme 1

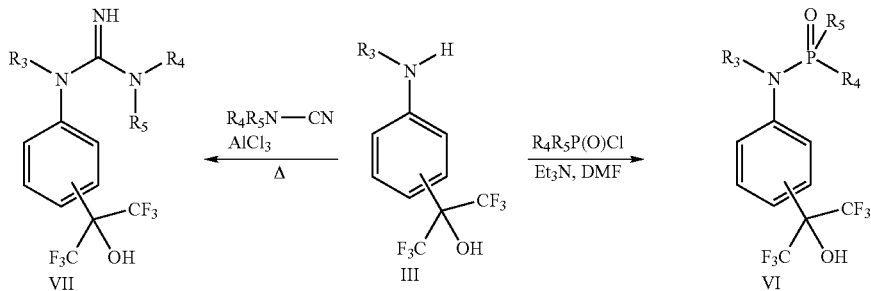

As shown in Scheme 1, aniline derivative II, which either is commercially available or prepared easily via literature procedure, was converted into its corresponding N-substituted phenylhexafluoroisopropanol aniline derivatives III. The latter were transformed into the corresponding urea IV, which is subsequently converted into the targeted molecule thioureas (V). Thioureas V could be also prepared directly from compound III via thiocarbamoyl chloride intermediate followed by the reaction with primary or secondary amines. When treated with cyanide or phosphoryl chloride, the aniline compound III gave the corresponding guanidines or phosphonamides respectively, under reaction conditions depicted in the above scheme.

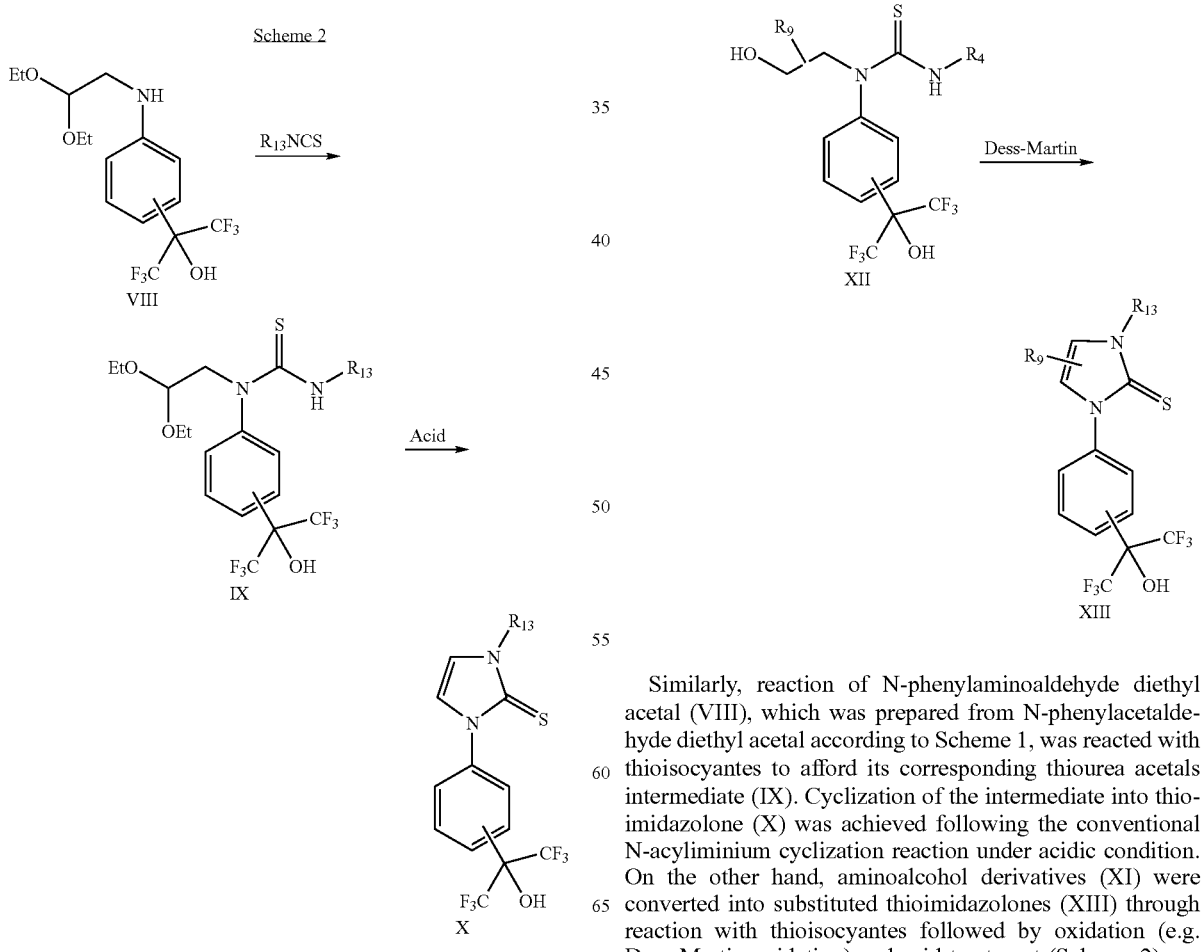

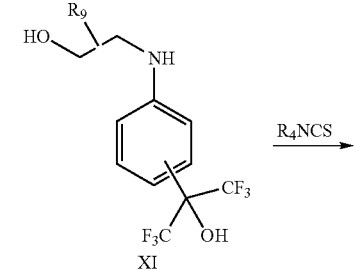

Similarly, reaction of N-phenylaminoaldehyde diethyl acetal (VIII), which was prepared from N-phenylacetaldehyde diethyl acetal according to Scheme 1, was reacted with thioisocyantes to afford its corresponding thiourea acetals intermediate (IX). Cyclization of the intermediate into thio-imidazolone (X) was achieved following the conventional N-acyliminium cyclization reaction under acidic condition. On the other hand, aminoalcohol derivatives (XI) were converted into substituted thioimidazolones (XIII) through reaction with thioisocyantes followed by oxidation (e.g. Dess-Martin oxidation) and acid treatment (Scheme 2).

Scheme 3

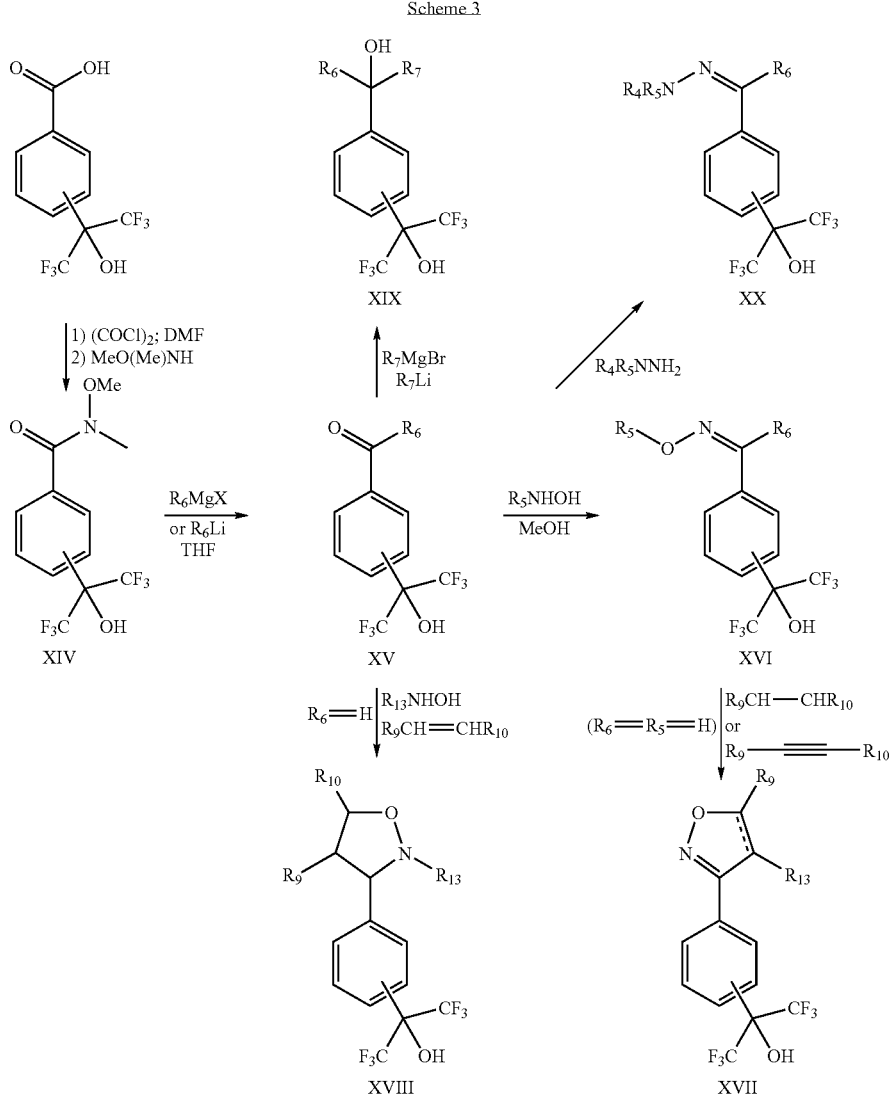

Non-cyclic or cyclic derivatives including ketones (XV), oximes (XVI), hydrazone/carbazide (XX), alcohols (XIX) and isoxazoles/isoxazolines/isoxazolidines (XVII, XVIII), were prepared via a common ketone/aldehyde intermediate (XV), which was prepared from the Weinreb amide XIV. Thus, reaction of ketones or aldehydes (XV) with hydroxylamine or alkoxylamine afforded the corresponding oximes (XVI). Subsequent 1,3-dipolar reaction of aldoxime (XVI, $R_3=R_4=H$) with olefines or acetylenes gave rise to Δ2-isoxazoline or isoxazole derivatives (XVII). Similarly, aldehyde intermediate (XV) was converted into isoxazolidine (XVIII) upon treatment with N-substituted hydroxylamine and dienophiles (olefines or acetylenes). On the other hand, treatment of intermediate (XV) with organolithium or Grignard reagents resulted in a secondary or tertiary alcohol derivative (XIX). Or, the ketone intermediate XV could be converted into hydrazones (XX) via the reaction with hydrazines.

Scheme 4

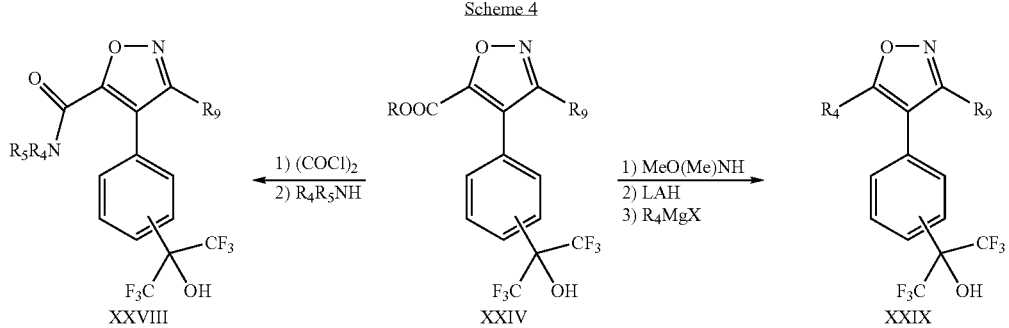

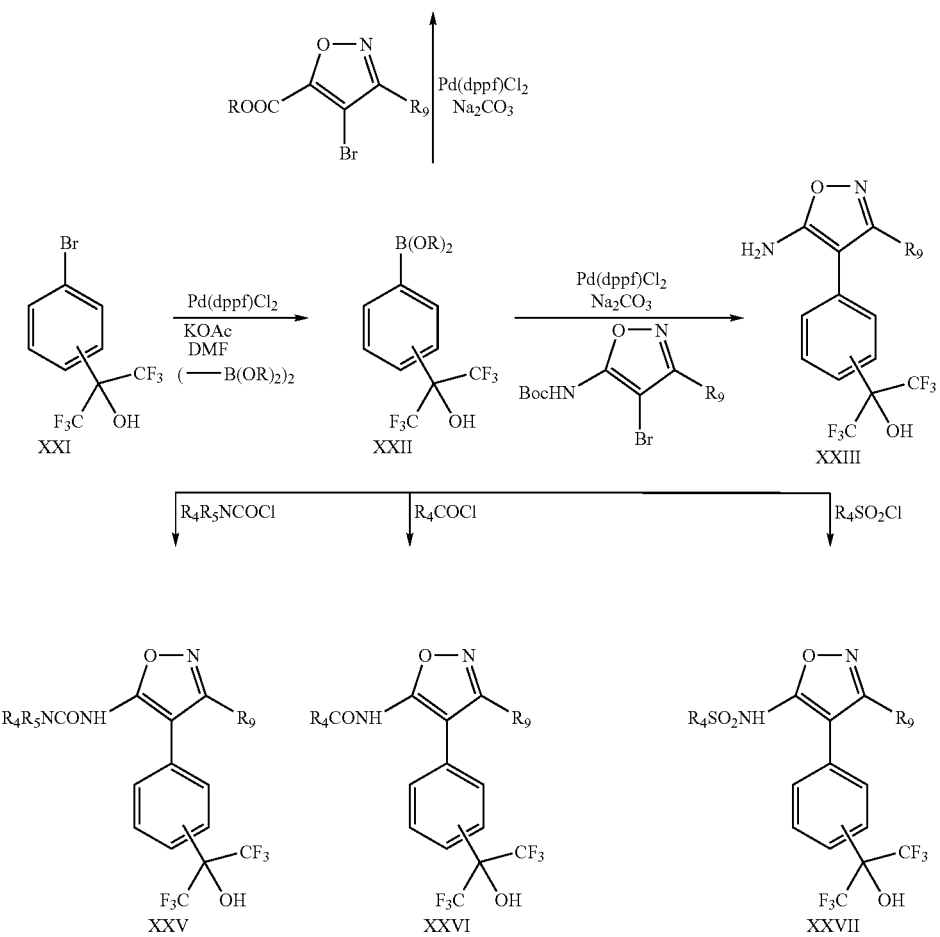
Scheme 4 summarizes the preparation of isoxazole related compounds. Thus, 2-hydroxyhexafluoroisoproyl-bromobenzene (XXI) was converted into the corresponding boronic acid (ester), which underwent Suzuki coupling with halogenated isoxazole compounds to provide XXIII or XXIV. Further modification led to compound XXV to XXIX as shown in Scheme 4.
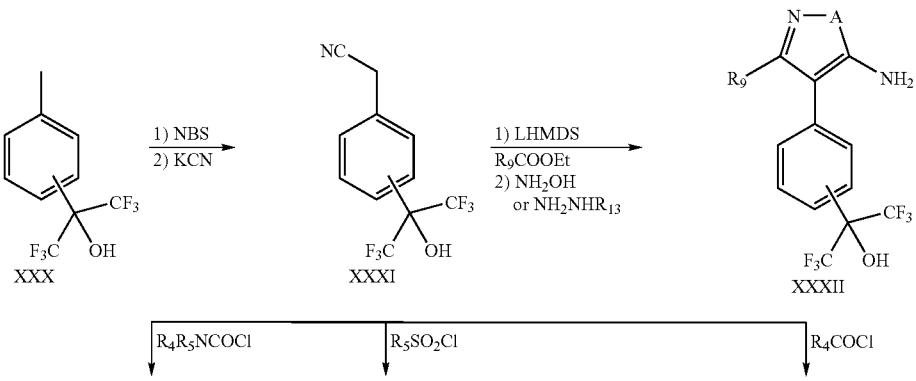

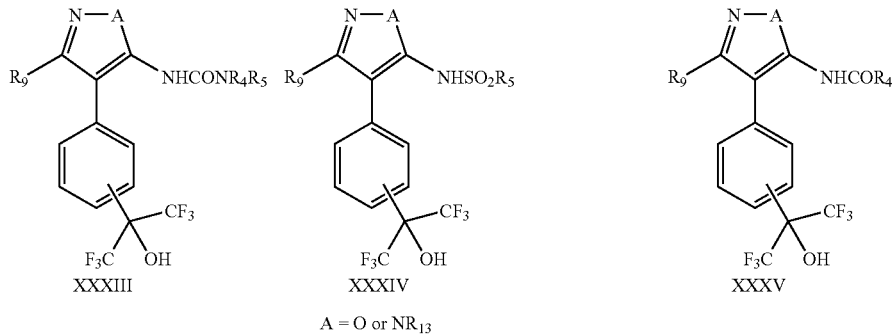

A = O or NR₁₃

An alternative synthetic route for preparing this type of isoxazole and pyrazole compounds are shown in Scheme 5. Tolyl-hexafluoro-2-hydroxyisopropanol XXX was first monobrominated to the corresponding benzyl bromide intermediate which was subsequently reacted with potassium cyanide to give rise to the benzyl nitrile compound XXXI. Reaction of the nitrile compound with ester in the presence of strong bases such as LDA to furnish the b-ketonitrile which upon treatment with hydroxylamine or substituted hydrazine gave the aminoisoxazole or aminopyrazole (XXXII) in good yields. Manipulation of the amino group led to the desired derivatives such as amides, ureas, sulfonamides and thioureas.

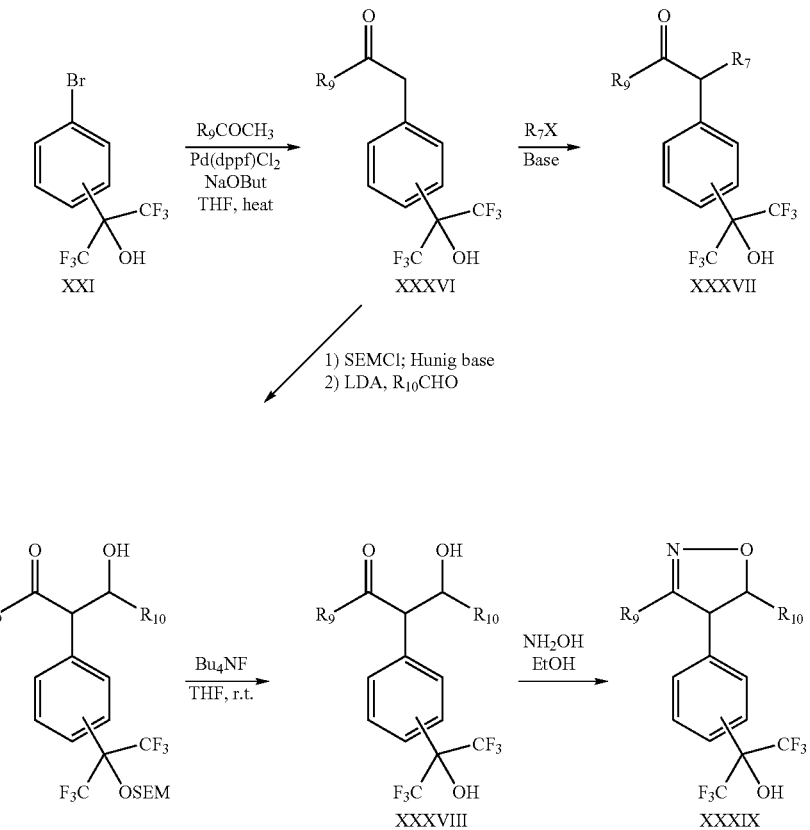

The corresponding isoxazoline derivatives were prepared according to the procedure described in Scheme 6. Buchwald-Hartwig reaction of bromobenzene derivative XXI with ketone in the presence of appropriate Pd catalyst and ligands provided the ketone intermediate XXXVI. Alkylation of the ketone product with halides or equivalent furnished the alkylated product XXXVII. The later could also be prepared directly from the starting material XXI using Buchwald-Hartwig conditions. On the other hand, aldol reaction of the ketone with aldehyde would provide the intermediate XXXVIII, which upon treatment with hydroxylamine gave the desired isoxazoline products XXXIX.

Scheme 7

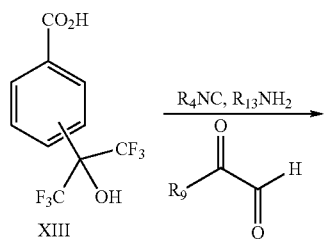

XIII

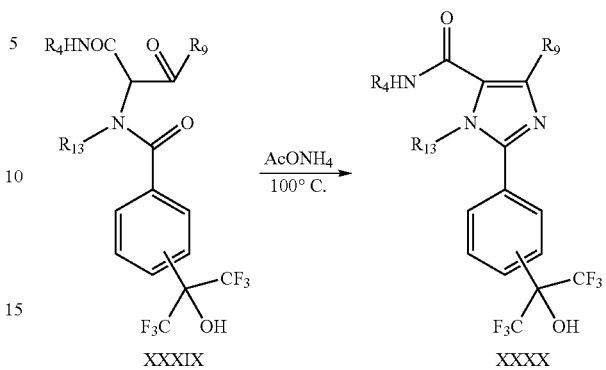

Scheme 7 described a synthesis of imidazole compounds. Ugi four component reaction of benzoic acid derivative XIII with isocyanide, amine and α-ketoaldehyde gave rise to a β-ketoamide intermediate XXXIX. The later underwent cyclization to give the desired imidazole compounds XXXX in the presence of ammonium acetate.

Scheme 8

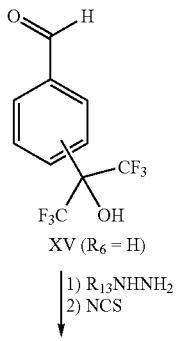

XV ($R_6$ = H)

1) $R_{13}NHNH_2$
2) NCS

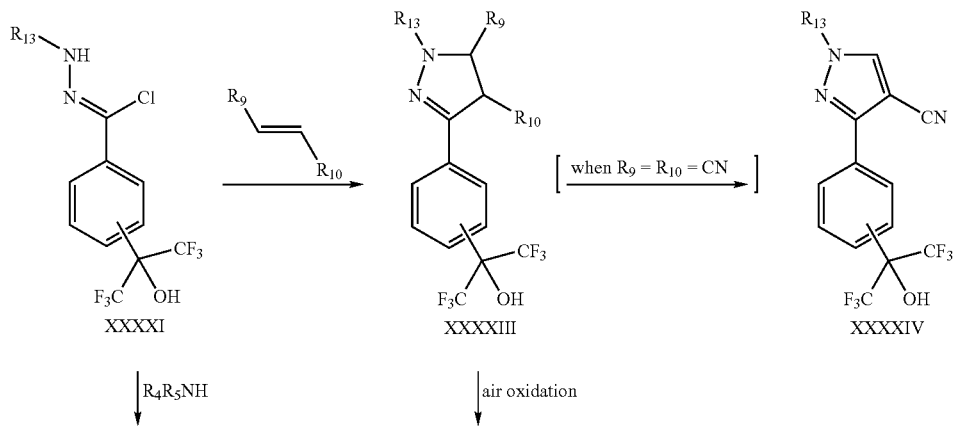

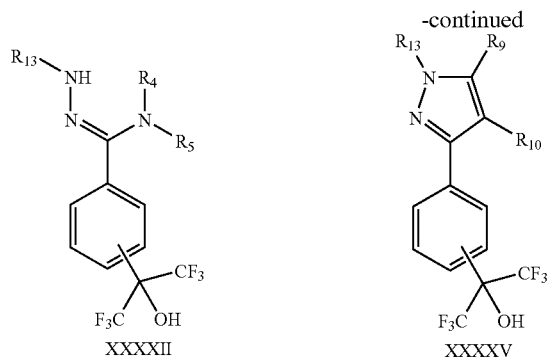

Scheme 8 described an example for preparation of opening chain compounds such as XXXXII or pyrazole/pyrizoline compounds. Thus the aldehyde XV was converted into halohydrazone such as chlorohydrazone XXXXI, which reacted with amine to give the open chain product XXXXII or to give pyrazoline compound XXXXII when it reacted with an olefin. The pyrazoline compounds could be oxidized into their corresponding pyrazoles XXXXV under oxidative conditions.

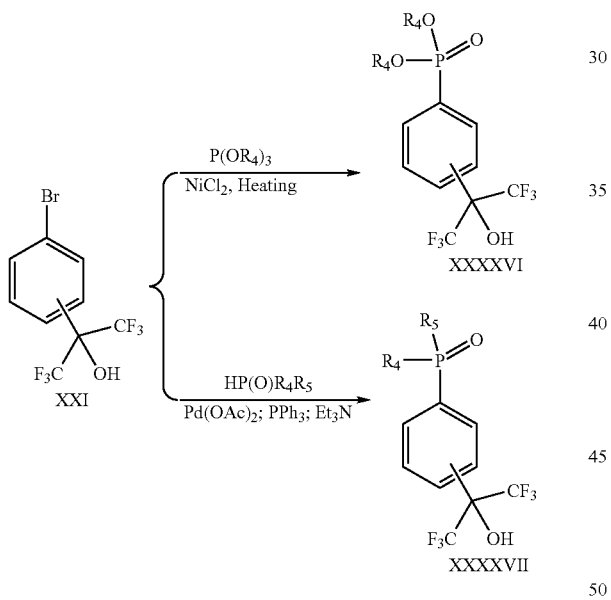

Phosphorus-containing compounds such as XXXXVI and XXXXVII were prepared from the brominated precursor XXI. Coupling of bromobenzene derivative with phosphite in the presence of NiCl$_2$ gave rise to the phosphorate derivative XXXXVI. In the presence of palladium catalyst, the coupling of bromobenzene derivative with phosphonate provided the phosphorus compound XXXXVII.

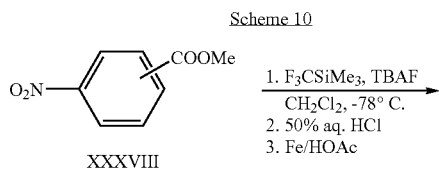

As shown in Scheme 10, trifluormethylketone derivatives were prepared from a commercially available nitrobenzoate XXXXVIII. Reaction of the nitrobenzoate with trifluoromethyl trimethyl silane provided the desired trifluormethyl ketone functionality. After reduction of the nitro group, the resulting aniline XXXXIX was converted into amide derivative L under the conventional conditions. Alkylation of anilide L was conducted in an indirect fashion. Thus, trifluoromethyl ketone functionality in L was reduced into its corresponding trifluoromethyl alcohol LII with NaBH$_4$. Subsequent alkylation with R$_4$X in the presence of NaH afforded the alkylated anilide LII. Oxidation of the alcohol intermediate gave the desired trifluoromethyl ketone product LIII.

Biological Activity

In vitro MCD Inhibitory Assay:

A spectrophotometric method for the determination of malonyl-CoA decarboxylase activity assay described in the literature, is adapted and modified for MCD inhibitory activity assay in a high-throughput format (Kolattukudy et al., *Methods in Enzymology* 71:150(1981)). The following reagents are added into a 96 well titer plate: Tris-HCl buffer, 20 µL, DTE, 10 µL; I-malate, 20 µL; NAD, 10 µL; NADH, 25 µL; water, 80 µL; malic dehydrogenase, 5 µL. The contents are mixed and incubated for 2 min followed by the addition of 5 µL of citrate synthase. The compound is added followed by 5 µL of malonyl-CoA decarboxylase prepared from rat heart and 20 µL of malonyl-CoA. The content is incubated and absorbence at 460 nM is measured.

Active compounds are characterized by the concentration of the compound that caused 50% inhibition of MCD activity ($IC_{50}$). The preferred compounds have the $IC_{50}$ value less than 10 µM. The most preferred compounds have the $IC_{50}$ value less than 100 nM.

TABLE I $IC_{50}$ of the MCD inhibitors

| Compound | $IC_{50}$ (µM) |
|---|---|
| Example 1 | 0.123 |
| Example 2 | 0.042 |
| Example 4 | 0.164 |
| Example 5-48 | 0.045 |
| Example 5-74 | 0.042 |
| Example 5-108 | 0.147 |
| Example 8-22 | 0.524 |
| Example 12 | 0.515 |
| Example 15 | 0.127 |
| Example 16 | 0.408 |
| Example 20-1 | 0.192 |
| Example 22 | 0.354 |
| Example 23-7 | 0.038 |
| Example 23-11 | 0.044 |
| Example 28 | 0.090 |
| Example 30 | 1.51 |

Glucose xidati n and Fatty Acid xidation Measurement in th perfus d Rat Heart:

Isolated working hearts from male Sprague-Dawley rats are subjected to a 60-minute aerobic perfusion period with a modified Krebs-Henseleit solution containing 5 mmol/L glucose; 100 µU/mL insulin; 3% BAS; and 1.2 mmol/L palmitate. Working hearts are used in these studies to approximate the metabolic demand of the heart seen in vivo. (Kantor et al:, Circulation Research 86:580-588(2000)). The test compound is added 5 minutes into the perfusion period.

Glucose oxidation rates are determined by the quantitative collection of $^{14}CO_2$ produced by hearts perfused with buffer containing [U14]-Glucose. Rates of fatty acid oxidation are determined by the quantitative collection of $^{14}CO_2$ produced by hearts perfused with buffer containing [$^{14}C$]palmitate (McNeill, J. H. in "*Measurement of cardiovascular function*", chapter 2, CRC press, New York (1997)).

Active compounds are characterized by an increase in glucose oxidation as compared to control experiment (DMSO). The compounds that caused statistically significant increases in glucose oxidation are considered to be active. The preferred compounds cause statistically significant increases in glucose oxidation at 20 µM. Statistical significance was calculated using the Student's t test for paired or unpaired samples, as appropriate. The results with $P<0.05$ are considered to be statistically significant.

EXAMPLES

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

$^1$H nuclear magnetic resonance spectra (NMR) is measured in $CDCl_3$ or other indicated solvents on a Varian NMR spectrometer (Unity Plus 400, 400 MHz for $^1$H) unless otherwise indicated and peak positions are expressed in parts per million (ppm) downfield from tetramethylsilane. The peak multiplicities are denoted as follows, s, singlet; d, doublet; t, triplet; m, multiplet.

The following abbreviations have the indicated meanings:
Ac=acetyl
Allyl=$CH_2$=$CH_2$—$CH_2$—
Bn=benzyl
CDI=carbonyl diimidazole
$CH_2Cl_2$ =dichloromethane
DIBAL=diisobutylaluminum hydride
DMAP=4-(dimethylamino)-pyridine
DMF=N,N-dimethylformamide
DMSO=dimethylsulfoxide
EDCl or EDAC=1-[3-(dimethylamino)propyl]-3-ethyl-carbodiimide hydrochloric acid
ESIMS=electron spray mass spectrometry
$Et_3N$=triethylamine
EtOAc=ethyl acetate
HMTA=hexamethylenetetramine
Lawesson's reagent=2,4-bis(4-methoxyphenyl)-1,3,2,4-dithiadiphosphetane-2,4-disulfide
LDA=lithium diisopropylamide
LHMDS=lithium bis(trimethylsilyl)amide
$MgSO_4$=magnesium sulfate
$NaHCO_3$=sodium bicarbonate
$Na_2CO_3$=sodium carbonate
NaH=sodium hydride
NBS=N-bromosuccinimide
NCS=N-chlorosuccinimide
$NH_4Cl$=ammonium chloride
Ph=phenyl
Py, or Pyr=pyridinyl
r.t.=room temperature
TFA=trifluoroacetic acid
THF=tetrahydrofuran
TLC=thin layer chromatography
TMS=trimethylsilyl
$Tf_2O$=triflic anhydride
Vinyl=$CH_2$=CH—
Alkyl group abbreviations
Me=methyl
Et=ethyl
n-Pr=normal propyl i-Pr=isopropyl
n-Bu=normal butyl
i-Bu=isobutyl
t-Bu=tertiary butyl
s-Bu=secondary butyl
c-Hex=cyclohexyl Example 1

Preparation of morpholine-4-carbothioic acid [4-(2,2,2-trifluoro-1-hydroxy-1-trifluoromethyl-ethyl)-phenyl]-(4-trifluoromethyl-benzyl)-amide

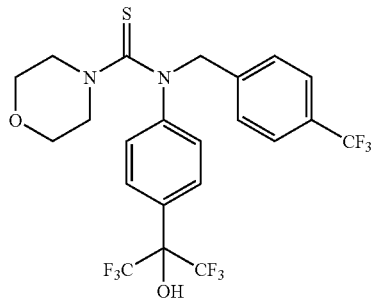

Step 1

To the solution of 2-(4-Amino-phenyl)-1,1,1,3,3,3-hexafluoro-propan-2-ol (200 mg, 0.77 mmol) and 4-morpholin carbonyl chloride (180 μL, 1.54 mmol) in pyridine (2 mL), is added DMAP (20 mg) at room temperature. After being heated at 90° C. for 2 hrs, the reaction mixture is diluted with ethyl acetate. The organic phase is washed with saturated $CuSO_4$ solution, 0.1 N HCl solution, saturated $NaHCO_3$ solution and brine, then dried over anhydrous $Na_2SO_4$. The solvent is removed under reduced pressure and the residue is purified by preparative TLC (Hexane:EtOAc, 2:1) to afford the urea intermediate as white solid (120 mg, 42%).

$^1$H NMR δ 3.45 (t, 4H), 3.74 (t, 4H), 4.92 (b, 1H), 6.46 (s, 2H), 7.36 (d, 2H) 7.61 (d, 2H); ESIMS: m/z 370.8 (M+H).

Step 2

To the solution of the urea intermediate (185 mg, 0.5 mmol) in DMF (5 mL), is added sodium hydride (100 mg, 2.5 mmol) at room temperature. The suspension is stirred for an additional 10 mins before being heated at 90° C. for 2 hrs. The reaction mixture is diluted with ethyl acetate. The organic phase is washed with water and dried over anhydrous $Na_2SO_4$. The solvent is removed under reduced pressure and the residue is purified by preparative TLC ($CH_2Cl_2$:MeCN, 10:1) to afford the alkylated intermediate as yellow oil (120 mg, 45%). $^1$H NMR δ3.21 (t, 4H), 3.51 (t, 4H), 4.91 (s, 2H), 5.12 (b, 1H), 7.11 (d, 2H), 7.39 (d, 2H), 7.55 (d, 2H), 7,64 (d, 2H); ESIMS: m/z 528.8 (M−H).

Step 3

The alkylated intermediate (110 mg, 0.207 mmol) and Lawesson's reagent (320 mg, 0.832 mmol) are mixed in toluene (3 mL) and the reaction mixture is heated at 120° C. for 6 hrs. The organic solvent is removed under reduced pressure and the residue is purified by preparative TLC ($CH_2Cl_2$:MeCN, 20:1) to afford the title compound as white foam (24 mg, 21%). $^1$H NMR δ3.52 (t, 4H), 3.66 (t, 4H), 4.94 (b, 1H), 5.48 (s, 2H), 7.09 (d, 2H), 7.46 (d, 2H), 7.58 (d, 2H), 7,68 (d, 2H); ESIMS: m/z 544.5 (M−H).

Example 2

Preparation of N-(4-cyanobutyl)-N-{4-[2,2,2-trifluoro-1-hydroxy-1-(trifluoromethyl)ethyl]phenyl}morpholine-4-carbothioamide

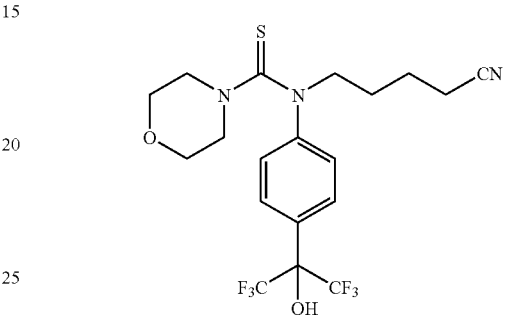

Step 1

To the solution of 2-(4-Amino-phenyl)-1,1,1,3,3,3-hexafluoro-propan-2-ol (200 mg, 0.77 mmol) and 4-morpholin carbonyl chloride (180 μL, 1.54 mmol) in pyridine (2 mL), is added DMAP (20 mg) at room temperature. After being heated at 90° C. for 2 hrs, the reaction mixture is diluted with ethyl acetate. The organic phase is washed with saturated $CuSO_4$ solution, 0.1 N HCl solution, saturated $NaHCO_3$ solution and brine, then dried over anhydrous $Na_2SO_4$. The solvent is removed under reduced pressure and the residue is purified by preparative TLC (Hexane:EtOAc, 2:1) to afford the urea intermediate as white solid (120 mg, 42%). $^1$H NMR δ 3.45 (t, 4H), 3.74 (t, 4H), 4.92 (b, 1H), 6.46 (s, 2H), 7.36 (d, 2H), 7.61 (d, 2H); ESIMS: m/z 370.8 (M+H).

Step 2

To the solution of the urea intermediate (110 mg, 0.3 mmol) in DMF (2 mL), is added sodium hydride (36 mg, 3 mmol) at room temperature. The suspension is stirred for an additional 10 mins before 5-bromovaleronitrile (42 μL, 0.4 mmol) was added. After being heated at 90° C. for 2 hrs, the reaction mixture is diluted with ethyl acetate. The organic phase is washed with water and dried over anhydrous $Na_2SO_4$. The solvent is removed under reduced pressure and the residue is purified by preparative TLC ($CH_2Cl_2$:MeCN, 10:1) to afford the alkylated intermediate as yellow oil (34 mg, 25%). $^1$H NMR 1.65 (m, 4H), 2.31 (t, 2H), 3.10 (t, 4H), 3.40 (t, 4H), 3.63 (t, 2H), 4.98 (s, 1H), 5.12 (b, 1H), 7.09 (d, 2H) 7,65 (d, 2H); ESIMS: m/z 450.8 (M−H).

Step 3

The alkylated intermediate (30 mg, 0.066 mmol) and Lawesson's reagent (107 mg, 0.266 mmol) are mixed in toluene (2 mL) and the reaction mixture is heated at 120° C. for 6 hrs. The organic solvent is removed under reduced pressure and the residue is purified by preparative TLC (CH₂Cl₂:MeCN, 20:1) to afford the title compound as white foam (21 mg, 68%). ¹H NMR δ1.73 (m, 2H), 1.86 (m, 2H), 2.4(t, 2H), 3.48 (t, 4H), 3.56 (t, 4H), 4.14(t, 2H), 4.23 (b, 1H), 7.11 (d, 2H) 7.72 (d, 2H); ESIMS: m/z 467.9 (M−H).

Example 3

Preparation of 1-butyl-3,3-dimethyl-1-[4-(2,2,2-trifluoro-1-hydroxy-1-trifluoromethyl-ethyl)-phenyl]-thiourea

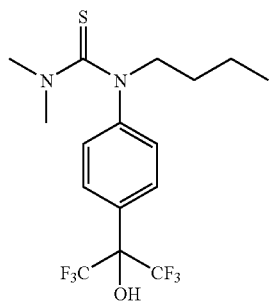

2-(4-Butylamino-phenyl)-1,1,1,3,3,3-hexafluoro-propan-2-ol and dimethylthio-carbamoyl chloride are mixed together in a sealed vial and heated at 150° C. for 10 min in a microwave. The reaction mixture is dissolved in dichloromethane and purified over preparative TLC (Acetonitrile:CH₂Cl₂=2:98) to give the title compound. ¹HNMR (CD₃OD) δ 0.95(t, 3H), 1.38(m, 2H), 1.65(m, 2H), 2.99 (s, 6H), 4.05(t, 2H), 4.90(s, 1H), 7.04(d, 2H), and 7.68(d, 2H); ESIMS m/z 401(M−H).

Example 4

Preparation of butyl {4-[2,2,2-trifluoro-1-hydroxy-1-(trifluoromethyl)ethyl]phenyl}amino)(diethylamino)methaniminium chloride

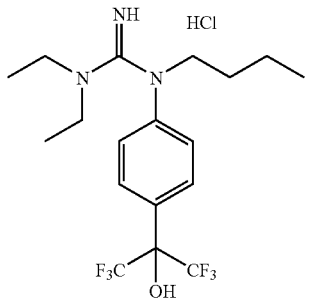

Aluminum chloride (81 mg, 0.603 mmol) is added to chlorobenzene (5 mL) containing diethylcyanamide (75 μL). The reaction mixture is stirred at r.t. under argon for 5 min before adding N-butyl-4[2,2,2-trifluoro-1-hydroxy-1-(trifluoromethyl) ethyl]benzenaminium chloride (200 mg; 0.57 mmol). The light yellow solution is heated at 140° C. for 3 days. The reaction mixture is evaporated and then directly purified by preparative TLC (MeOH:CHCl₃ 15:85) to afford the title compound as colorless solid (120 mg, 46.9%). m.p. 217.1-219.2° C. (dec). ¹H NMR δ0.84 (m, 9H), 1.17 (m, 2H), 1.55 (m, 2H), 3.17 (m, 4H), 3.71 (t, 2H), 7.03 (d, 2H), 7.68 (d, 2H), ESIMS: m/z 414 (M+H).

Example 5

TABLE 1

The following compounds are prepared in accordance with the procedure described as in the above examples

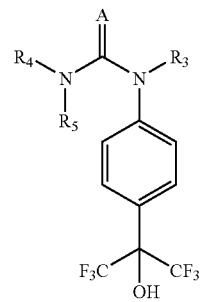

| Example | R₄ | R₅ | R₃ | A |
|---|---|---|---|---|
| Example 5-1 | | —(CH₂)₄— | -Et | S |
| Example 5-2 | | —(CH₂)₄— | -nBu | S |
| Example 5-3 | | —(CH₂)₄— | -nBu | NH |
| Example 5-4 | | —(CH₂)₄— | MeO₂C(CH₂)₄— | S |
| Example 5-5 | | —(CH₂)₄— | HOOC(CH₂)₄— | S |
| Example 5-6 | | —(CH₂)₅— | -Et | S |
| Example 5-7 | | —(CH₂)₅— | -nPr | NH |
| Example 5-8 | | —(CH₂)₅— | -nBu | NH |
| Example 5-9 | 1-Morpholin-CH₂CH₂— | —CH₂CH₂OH | -nPr | S |
| Example 5-10 | 1-Morpholinyl-CH₂CH₂— | —CH₂CH₂OH | -nBu | S |
| Example 5-11 | 1-Morpholinyl-CH₂CH₂CH₂— | CN—CH₂CH₂— | -nPr | S |

TABLE 1-continued

The following compounds are prepared in accordance with the procedure described as in the above examples

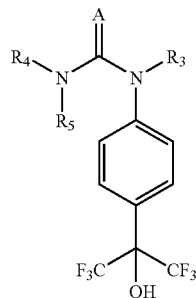

| Example | R4 | R5 | R3 | A |
|---|---|---|---|---|
| Example 5-12 | 1-Morpholinyl-CH$_2$CH$_2$CH$_2$— | CN—CH$_2$CH$_2$— | -nBu | S |
| Example 5-13 | 1-Piperidinyl- | —H | -Et | S |
| Example 5-14 | 1-Piperidinyl- | —H | -nPr | S |
| Example 5-15 | 2,4-difluorophenyl- | —H | -Me | S |
| Example 5-16 | 2,6-difluoro-Ph- | —H | -Me | S |
| Example 5-17 | 2,6-dimethoxy-Ph- | —H | -Me | S |
| Example 5-18 | 2-F-4-Br-Ph- | —H | -Me | S |
| Example 5-19 | -2-Py | -Bn | -Et | S |
| Example 5-20 | 2-ThienylCH$_2$CH$_2$— | —H | -Me | S |
| Example 5-21 | 3,5-bis(CF$_3$)-Ph- | —H | -Me | S |
| Example 5-22 | 3,5-dimethyl-4-isoxazolyl- | —H | -Me | S |
| Example 5-23 | 4-Br-2,6-dimethyl-Ph- | —H | -Me | S |
| Example 5-24 | -Allyl | —H | -Me | S |
| Example 5-25 | -Bn | —H | —H | S |
| Example 5-26 | -Bn | —H | -Me | S |
| Example 5-27 | -Bn | -Me | -Me | S |
| Example 5-28 | -Bn | -Me | -Et | S |
| Example 5-29 | —CH$_2$CH$_2$CH(Bn)CH$_2$CH$_2$— | | -Et | S |
| Example 5-30 | —CH$_2$CH$_2$CH(CH$_2$CH$_2$OH)CH$_2$CH$_2$— | | -nBu | S |
| Example 5-31 | —CH$_2$CH$_2$CH(CH$_2$OH)CH$_2$CH$_2$— | | -nBu | S |
| Example 5-32 | —CH$_2$CH$_2$CH$_2$CH(CH$_2$OH)CH$_2$— | | -nBu | S |
| Example 5-33 | —CH$_2$CH$_2$OCH$_2$CH$_2$— | | -Me | S |
| Example 5-34 | —CH$_2$CH$_2$OCH$_2$CH$_2$— | | -Et | S |
| Example 5-35 | —CH$_2$CH$_2$OCH$_2$CH$_2$— | | -nPr | S |
| Example 5-36 | —CH$_2$CH$_2$OCH$_2$CH$_2$— | | —CH$_2$CH$_2$OH | S |
| Example 5-37 | —CH$_2$CH$_2$OCH$_2$CH$_2$— | | —H | S |
| Example 5-38 | —CH$_2$CH$_2$OCH$_2$CH$_2$— | | n-Pentyl- | S |
| Example 5-39 | —CH$_2$CH$_2$OCH$_2$CH$_2$— | | n-Hexyl- | S |
| Example 5-40 | —CH$_2$CH$_2$OCH$_2$CH$_2$— | | n-Haptyl- | S |
| Example 5-41 | —CH$_2$CH$_2$OCH$_2$CH$_2$— | | -nBu | S |
| Example 5-42 | —CH$_2$CH$_2$OCH$_2$CH$_2$— | | n-Octyl- | S |
| Example 5-43 | —CH$_2$CH$_2$OCH$_2$CH$_2$— | | i-PrCH$_2$CH$_2$— | S |
| Example 5-44 | —CH$_2$CH$_2$OCH$_2$CH$_2$— | | c-Hexyl-CH$_2$CH$_2$— | S |
| Example 5-45 | —CH$_2$CH$_2$OCH$_2$CH$_2$— | | -Et | S |
| Example 5-46 | —CH$_2$CH$_2$OCH$_2$CH$_2$— | | CN(CH$_2$)$_3$— | S |
| Example 5-47 | —CH$_2$CH$_2$OCH$_2$CH$_2$— | | AcO(CH$_2$)$_4$— | S |
| Example 5-48 | —CH$_2$CH$_2$OCH$_2$CH$_2$— | | MeO$_2$C(CH$_2$)$_4$— | S |
| Example 5-49 | —CH$_2$CH$_2$OCH$_2$CH$_2$— | | HO(CH$_2$)$_4$— | S |
| Example 5-50 | —CH$_2$CH$_2$OCH$_2$CH$_2$— | | HOOC(CH$_2$)$_4$— | S |
| Example 5-51 | —CH$_2$CH$_2$OCH$_2$CH$_2$— | | EtO$_2$CCH$_2$CH$_2$CH$_2$— | NH |
| Example 5-52 | —CH$_2$CH$_2$OCH$_2$CH$_2$— | | PhCH$_2$CH$_2$— | S |
| Example 5-53 | —CH$_2$CH$_2$OCH$_2$CH$_2$— | | -nBu | NH |
| Example 5-54 | —CH$_2$CH$_2$OCH$_2$CH$_2$— | | MeO$_2$CCH$_2$— | S |
| Example 5-55 | —CH$_2$CH$_2$OCH$_2$CH$_2$— | | EtO$_2$C(CH$_2$)$_5$— | S |
| Example 5-56 | —CH$_2$CH$_2$OCH$_2$CH$_2$— | | HOOC(CH$_2$)$_5$— | S |
| Example 5-57 | —CH$_2$CH$_2$OCH$_2$CH$_2$— | | EtO$_2$C(CH$_2$)$_6$— | S |
| Example 5-58 | —CH$_2$CH$_2$OCH$_2$CH$_2$— | | CN—(CH$_2$)$_5$— | S |
| Example 5-59 | —CH$_2$CH$_2$OCH$_2$CH$_2$— | | HOOC(CH$_2$)$_6$— | S |
| Example 5-60 | —CH$_2$CH$_2$OCH$_2$CH$_2$— | | 5-Tetrazolyl-CH$_2$CH$_2$CH$_2$CH$_2$— | S |
| Example 5-61 | —CH$_2$CH$_2$OCH$_2$CH$_2$— | | MeO$_2$CCH$_2$CH$_2$— | S |
| Example 5-62 | —CH$_2$CH$_2$OCH$_2$CH$_2$— | | MeO$_2$C(CH$_2$)$_3$— | S |
| Example 5-63 | —CH$_2$CH$_2$OCH$_2$CH$_2$— | | HOOCCH$_2$CH$_2$— | S |
| Example 5-64 | —CH$_2$CH$_2$OCH$_2$CH$_2$— | | HOOCCH$_2$CH$_2$CH$_2$— | S |
| Example 5-65 | —CH$_2$CH$_2$OCH$_2$CH$_2$— | | MeO$_2$C(CH$_2$)$_4$— | S |

TABLE 1-continued

The following compounds are prepared in accordance with the procedure described as in the above examples

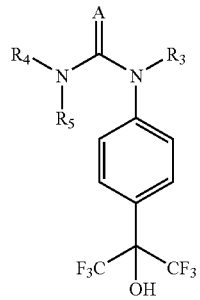

| Example | R$_4$ | R$_5$ | R$_3$ | A |
|---|---|---|---|---|
| Example 5-66 | | —CH$_2$CH$_2$OCH$_2$CH$_2$— | 4-Py-CH$_2$— | S |
| Example 5-67 | | —CH$_2$CH$_2$OCH$_2$CH$_2$— | P—CF$_3$-PhCH$_2$— | S |
| Example 5-68 | | —CH$_2$CH$_2$OCH$_2$CH$_2$— | 3-PyCH$_2$— | NH |
| Example 5-69 | | —CH$_2$CH$_2$OCH$_2$CH$_2$— | 3-PyCH$_2$— | S |
| Example 5-70 | | —CH$_2$CH$_2$OCH$_2$CH$_2$— | 2-Py-CH$_2$— | S |
| Example 5-71 | | —CH$_2$CH$_2$OCH$_2$CH$_2$— | 2-Py-CH$_2$— | S |
| Example 5-72 | | —CH$_2$CH$_2$OCH$_2$CH$_2$— | FCH$_2$CH$_2$CH$_2$— | S |
| Example 5-73 | | —CH$_2$CH$_2$OCH$_2$CH$_2$— | P—CF$_3$-PhCH$_2$— | S |
| Example 5-74 | | —CH$_2$CH$_2$OCH$_2$CH$_2$— | CN—(CH$_2$)$_4$— | S |
| Example 5-75 | | —CH$_2$CH$_2$OCH$_2$CH$_2$— | MeC(=CH$_2$)CH$_2$— | S |
| Example 5-76 | | —CH$_2$CH$_2$OCH$_2$CH$_2$— | 1-Pyrrolyl(CH$_2$)$_3$— | NH |
| Example 5-77 | | —CH$_2$CH$_2$OCH$_2$CH$_2$— | 1-Pyrrolyl(CH$_2$)$_3$— | S |
| Example 5-78 | | —CH$_2$CH$_2$OCH$_2$CH$_2$— | t-Bu-CCCH=CHCH$_2$— | S |
| Example 5-79 | | —CH$_2$CH$_2$OCH$_2$CH$_2$— | CHC≡CH$_2$— | S |
| Example 5-80 | | —CH$_2$CH$_2$OCH$_2$CH$_2$— | p-CN-Bn | S |
| Example 5-81 | | —CH$_2$CH$_2$OCH$_2$CH$_2$— | MeC≡CCH$_2$— | S |
| Example 5-82 | | —CH$_2$CH$_2$OCH$_2$CH$_2$— | MeCH$_2$C≡CCH$_2$— | S |
| Example 5-83 | | —CH$_2$CH$_2$OCH$_2$CH$_2$— | p-CN-Bn | S |
| Example 5-84 | —CH$_2$CH$_2$OH | -Et | -Et | S |
| Example 5-85 | —CH$_2$CH$_2$OH | —CH$_2$CH$_2$OH | -Et | S |
| Example 5-86 | —CH$_2$CH$_2$OH | —CH$_2$CH$_2$OH | -nBu | S |
| Example 5-87 | —CH$_2$CH$_2$OH | -Et | -nBu | S |
| Example 5-88 | —CH$_2$CONH$_2$ | -Et | -nPr | S |
| Example 5-89 | —CH$_2$CONH$_2$ | -Et | -nBu | S |
| Example 5-90 | —CH$_2$CONH$_2$ | -Et | MeO$_2$CCH$_2$— | S |
| Example 5-91 | CN—CH$_2$CH$_2$— | -Et | -Et | S |
| Example 5-92 | CN—CH$_2$CH$_2$— | -Et | MeO$_2$C(CH$_2$)$_4$— | S |
| Example 5-93 | CN—CH$_2$CH$_2$— | -Et | HOOC(CH$_2$)$_4$— | S |
| Example 5-94 | —CO$_2$Et | —H | -Me | S |
| Example 5-95 | —CO$_2$Et | —H | —H | S |
| Example 5-96 | c-Pr-CH$_2$— | -nPr | -Et | S |
| Example 5-97 | c-Pr-CH$_2$— | 4-Cl-6-Me-PhCH$_2$CH$_2$— | -Et | S |
| Example 5-98 | -Cyclohex | —H | —H | S |
| Example 5-99 | -Cyclohex | —H | -Me | S |
| Example 5-100 | -Cyclohex | -Et | -Et | S |
| Example 5-101 | -Cyclohex | -Et | -nBu | S |
| Example 5-102 | -Cyclohex | -Et | MeO$_2$C(CH$_2$)$_4$— | S |
| Example 5-103 | -Cyclohex | -Et | HOOC(CH$_2$)$_4$— | S |
| Example 5-104 | -Et | —H | -Me | S |
| Example 5-105 | -Et | —H | -Et | S |
| Example 5-106 | -Et | -Et | -Et | S |
| Example 5-107 | -Et | -Et | -nPr | S |
| Example 5-108 | -Et | -Et | -nBu | S |
| Example 5-109 | -Et | -Et | -nBu | NHCN |
| Example 5-110 | -Et | -Et | -nBu | NH |
| Example 5-111 | -Et | -Et | MeO$_2$C(CH$_2$)$_4$— | S |
| Example 5-112 | -Et | -Et | HOOC(CH$_2$)$_4$— | S |
| Example 5-113 | EtO$_2$CCH$_2$— | —H | -Me | S |
| Example 5-114 | EtO$_2$CCH$_2$— | EtO$_2$CCH$_2$— | -nPr | S |
| Example 5-115 | EtO$_2$CCH$_2$— | EtO$_2$CCH$_2$— | -nBu | S |
| Example 5-116 | Fmoc- | —H | —H | S |

TABLE 1-continued

The following compounds are prepared in accordance with the procedure described as in the above examples

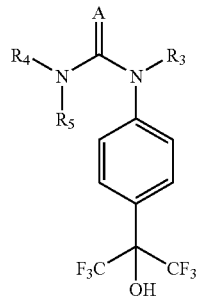

| Example | R$_4$ | R$_5$ | R$_3$ | A |
|---|---|---|---|---|
| Example 5-117 | Fmoc- | —H | -Et | S |
| Example 5-118 | —H | —H | -nBu | NH |
| Example 5-119 | HO(CH$_2$)$_4$— | -Et | -Et | S |
| Example 5-120 | HO(CH$_2$)$_4$— | -Et | -nPr | S |
| Example 5-121 | HO(CH$_2$)$_4$— | -Et | -nBu | S |
| Example 5-122 | HO(CH$_2$)$_4$— | -Et | MeO$_2$CCH$_2$— | S |
| Example 5-123 | HO(CH$_2$)$_4$— | -Et | MeO$_2$C(CH$_2$)$_4$— | S |
| Example 5-124 | HO(CH$_2$)$_4$— | -Et | HOOC(CH$_2$)$_4$— | S |
| Example 5-125 | HO(CH$_2$)$_4$— | -Et | EtO$_2$C(CH$_2$)$_5$— | S |
| Example 5-126 | HO(CH$_2$)$_4$— | -Et | HOOC(CH$_2$)$_5$— | S |
| Example 5-127 | HO(CH$_2$)$_4$— | -Et | EtO$_2$C(CH$_2$)$_6$— | S |
| Example 5-128 | HO(CH$_2$)$_4$— | -nBu | -nBu | S |
| Example 5-129 | HO(CH$_2$)$_4$— | -Et | CN—(CH$_2$)$_4$— | S |
| Example 5-130 | HO(CH$_2$)$_4$— | -Et | HOOC(CH$_2$)$_6$— | S |
| Example 5-131 | HO(CH$_2$)$_4$— | -Et | MeO$_2$CCH$_2$CH$_2$— | S |
| Example 5-132 | HO(CH$_2$)$_4$— | -Et | MeO$_2$C(CH$_2$)$_3$— | S |
| Example 5-133 | HO(CH$_2$)$_4$— | -Et | HOOCCH$_2$CH$_2$— | S |
| Example 5-134 | HO(CH$_2$)$_4$— | -Et | HOOCCH$_2$CH$_2$CH$_2$— | S |
| Example 5-135 | HO(CH2)$_6$— | -Me | -nBu | S |
| Example 5-136 | HOCH$_2$CH(Et)- | —H | —H | S |
| Example 5-137 | HOCH$_2$CH(i-Pr)- | —H | —H | S |
| Example 5-138 | HOCH$_2$CH(OH)CH$_2$— | -Me | -nBu | S |
| Example 5-139 | HOCH$_2$CH$_2$CH$_2$— | —CH$_2$CH$_2$OH | -nPr | S |
| Example 5-140 | HOCH$_2$CH$_2$CH$_2$— | —CH$_2$CH$_2$OH | -nBu | S |
| Example 5-141 | HOOCCH$_2$— | HOOCCH$_2$— | -nBu | S |
| Example 5-142 | -iBu | -Me | -Et | S |
| Example 5-143 | -iBu | -iBu | -Et | S |
| Example 5-144 | i-Pr- | i-Pr- | —H | NH |
| Example 5-145 | i-Pr- | i-Pr- | -nBu | NH |
| Example 5-146 | m-BrPh- | —H | -Me | S |
| Example 5-147 | -Me | -Me | -Et | S |
| Example 5-148 | -Me | -Me | -nPr | S |
| Example 5-149 | -Me | -Me | -nPr | NH |
| Example 5-150 | -Me | -Me | -nBu | S |
| Example 5-151 | -Me | -Me | MeO$_2$CCH$_2$— | S |
| Example 5-152 | Me$_2$N(+)(CH$_2$)$_3$— | Me$_2$N(+)CH$_2$CH$_2$CH$_2$— | -nPr | S |
| Example 5-153 | Me$_2$NCH$_2$CH$_2$— | -Et | -Et | S |
| Example 5-154 | Me$_2$NCH$_2$CH$_2$CH$_2$— | Me$_2$NCH$_2$CH$_2$CH$_2$— | -nPr | S |
| Example 5-155 | MeC(OH)(Me)CH$_2$— | -Et | -Et | S |
| Example 5-156 | MeCH(OH)CH$_2$— | —H | —H | S |
| Example 5-157 | MeOCH$_2$CH$_2$— | -Et | -Et | S |
| Example 5-158 | MeOCH$_2$CH$_2$— | -Et | —H | NH |
| Example 5-159 | MeOCH$_2$CH$_2$— | -Et | —H | NH |
| Example 5-160 | MeOCH$_2$CH$_2$— | -Et | —H | NH |
| Example 5-161 | m-NO$_2$Ph- | —H | -Me | S |
| Example 5-162 | m-NO$_2$PhCOOCH$_2$CH$_2$— | -iBu | -Et | S |
| Example 5-163 | m-Tolyl- | —H | -Me | S |
| Example 5-164 | -nBu | -nBu | -nBu | NH |
| Example 5-165 | —NMe$_2$ | —H | -Et | S |
| Example 5-166 | —NMe$_2$ | —H | -nPr | S |

TABLE 1-continued

The following compounds are prepared in accordance with the procedure described as in the above examples

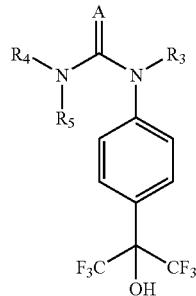

| Example | R4 | R5 | R3 | A |
|---|---|---|---|---|
| Example 5-167 | -nPr | —H | -Me | S |
| Example 5-168 | -nPr | -Me | -Et | S |
| Example 5-169 | -nPr | -Me | -nPr | S |
| Example 5-170 | -nPr | —CH$_2$CH$_2$OH | -nBu | S |
| Example 5-171 | o-BrPh- | —H | -Me | S |
| Example 5-172 | o-EtOPh- | —H | -Me | S |
| Example 5-173 | o-FPh- | —H | -Me | S |
| Example 5-174 | o-MeO$_2$CPh- | —H | -Me | S |
| Example 5-175 | o-MeOPh- | —H | -Me | S |
| Example 5-176 | o-MeSPh- | —H | -Me | S |
| Example 5-177 | o-NO$_2$Ph- | —H | -Me | S |
| Example 5-178 | o-Tolyl- | —H | -Me | S |
| Example 5-179 | p-BrPh- | —H | —H | S |
| Example 5-180 | p-BrPh- | —H | -Me | S |
| Example 5-181 | p-CF$_3$Ph- | —H | —H | S |
| Example 5-182 | p-CF$_3$Ph- | —H | -Me | S |
| Example 5-183 | p-EtO$_2$C-Ph- | —H | -Me | S |
| Example 5-184 | p-EtOPh- | —H | -Me | S |
| Example 5-185 | p-FBn- | —H | -Me | S |
| Example 5-186 | p-FPh | —H | —H | S |
| Example 5-187 | p-FPh | —H | -Me | S |
| Example 5-188 | Ph- | —H | —H | S |
| Example 5-189 | Ph- | —H | -Me | NH |
| Example 5-190 | Ph- | —H | -Me | S |
| Example 5-191 | Ph- | -Et | -Me | S |
| Example 5-192 | Ph- | -Et | -Et | S |
| Example 5-193 | Ph- | -Me | -Et | S |
| Example 5-194 | Ph- | -Allyl | -Et | S |
| Example 5-195 | Ph- | -nBu | -Et | S |
| Example 5-196 | Ph- | -Bn | -Et | S |
| Example 5-197 | Ph- | CN—CH$_2$CH$_2$— | -Et | S |
| Example 5-198 | PhCH$_2$CH$_2$— | —H | -Me | S |
| Example 5-199 | PhCH$_2$CH$_2$— | -Me | -Et | S |
| Example 5-200 | Ph-N(Me)- | —H | -Et | S |
| Example 5-201 | p-MeC(=CH$_2$)-Ph-C(Me)$_2$— | —H | -Me | S |
| Example 5-202 | p-MeO$_2$CPh- | -Me | -Et | S |
| Example 5-203 | p-MeSPh- | —H | -Me | S |
| Example 5-204 | p-NO$_2$Ph- | —H | -Me | S |
| Example 5-205 | p-Tolyl- | —H | -Me | S |

Example 6

Preparation of 1-(4-{2,2,2-trifluoro-1-hydroxy-1-trifluoromethyl)phenyl}-butan-1-one

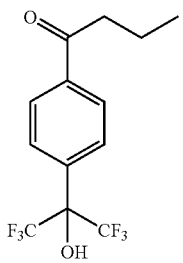

Step 1
A few drops of DMF are added to a solution of benzoic acid (5 g, 17.4 mmol) and oxalyl chloride (10 mL, 20 mmol) in dichlormethane at 0° C. The reaction mixture is stirred at room temperature for 14 hours. The solvents are removed under reduced pressure to afford the acyl chloride.

Step 2
The acyl chloride obtained above in acetone (25 mL) is added to a solution of N,O-dimethyl hydroxyamine (20 mmol) in saturated $Na_2CO_3$ (25 mL) at room temperature. The reaction mixture is stirred at the temperature for 16 hours and acidified with concentrated HCl. The organic solvent is removed under reduced pressure and the aqueous layer is extracted with EtOAc. The combined organic extract is washed with 1N HCl, saturated $NaHCO_3$ and brine and dried over $MgSO_4$. After removal the solvent, the N-methoxymethyl amide (Weinreb amide) is obtained in pure form (5.8 g).

Step 3
n-Propylmagnesium bromide (3 mL) is added to a solution of the Weinreb amide intermediate obtained above (662 mg, 2 mmol) in THF (6 mL) at 0° C. under an argon atmosphere. The reaction mixture is stirred at 0° C. for 30 minutes and then at the room temperature for 4 hours. The reaction mixture is poured into ice cold 1N HCl and extracted with EtOAc. The combined organic solvent is washed with saturated $NaHCO_3$, brine and dried over $MgSO_4$. The solvent is removed under reduced pressure to afford the title compound (620.7 mg). $^1$H NMR δ1.00 (t, 3H), 1.78 (qt, 2H), 2.95 (t, 2H), 7.80 (d, 2H), 8.00 (d, 2H); ESIMS: m/z 313 (M–H).

Example 7

Preparation of 1-{4-[2,2,2-trifluoro-1-hydroxy-1-(trifluoromethyl)ethyl]phenyl}butan-1-one oxime

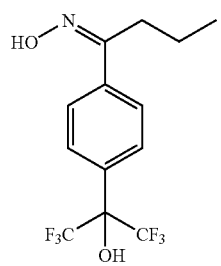

1-(4-{2,2,2-trifluoro-1-hydroxy-1-trifluoromethyl)phenyl}-butan-1-one (47 mg; cf. Example 6) and hydroxyamine (52 mg) are mixed in EtOH (2 mL). The mixture is stirred at room temperature for 12 hours. The solvent is removed under reduced pressure and the residue is purified by preparative TLC to afford the title compound (20.5 mg). $^1$H NMR ($CD_3OD$) δ0.98 (t, 3H), 1.46 (qt, 2H), 2.78 (t, 2H), 7.70 (m, 4H); ESIMS: m/z 330 (M+H).

Example 8

TABLE 2

The following ketone and oxime compounds are prepared in accordance with the procedure as described in the above examples.

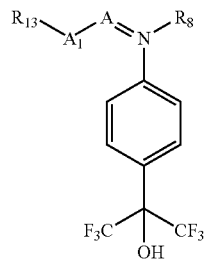

| Example | A | $A_1$ | $R_{13}$ | $R_8$ |
|---|---|---|---|---|
| Example 8-1 | O | — | — | i-Bu |
| Example 8-2 | O | — | — | i-Pr |
| Example 8-3 | O | — | — | n-Pentyl |
| Example 8-4 | O | — | — | Vinyl |
| Example 8-5 | O | — | — | Phenyl |
| Example 8-6 | O | — | — | 2-Pyridinyl |
| Example 8-7 | O | — | — | 3-Pyridinyl |
| Example 8-8 | O | — | — | 4-Pyridinyl |
| Example 8-9 | O | — | — | Me-CH=CH— |
| Example 8-10 | O | — | — | Pr-C≡C— |
| Example 8-11 | N | O | H | i-Bu |
| Example 8-12 | N | O | H | i-Pr |
| Example 8-13 | N | O | H | n-Pentyl |
| Example 8-14 | N | O | H | $CH_2$=CH— |
| Example 8-15 | N | O | H | Phenyl |
| Example 8-15 | N | O | H | 4-Pyridinyl |
| Example 8-16 | N | O | H | n-PrC≡C— |
| Example 8-17 | N | O | Me | n-Bu |
| Example 8-17 | N | O | Bn | n-Pr |
| Example 8-18 | N | O | Et | n-Pr |
| Example 8-19 | N | O | t-Bu | n-Pr |
| Example 8-20 | N | O | Ph | n-Pr |
| Example 8-21 | N | O | $PhOCH_2CH_2$— | n-Pr |
| Example 8-22 | N | O | Morpholinyl-$COCH_2$— | n-Pr |
| Example 8-23 | N | O | i-Pr | n-Pr |

Example 9

Preparation of 1,1,1,3,3,3-hexafluoro-2-(4-{1-[(2-furylmethyl)amino]butyl}phenyl)propan-2-ol

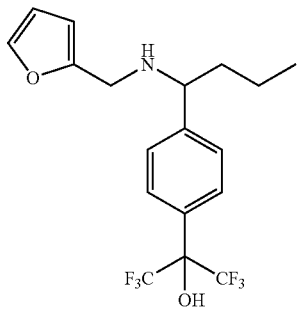

1-(4-{2,2,2-Trifluoro-1-hydroxy-1-trifluoromethyl)phenyl}-butan-1-one (237 mg, 0.75 mmol, cf. Example 6) and furfuryl amine (0.08 mL) in MeOH (3 mL) are treated with solid NaBH₃CN (94 mg, 1.5 mmol) followed by HOAc (0.1 mL) at room temperature. The reaction mixture is stirred overnight. The solvent is removed and the residue is re-dissolved in EtOAc. The organic layer is washed with 1NHCl, saturated NaHCO₃ and brine and dried over MgSO₄. The desired product (33.7 mg) is obtained after purification by preparative TLC (acetonitrile:CH₂Cl₂, 3:97). ¹H NMR δ0.80 (t, 3H), 1.20 (m, 2H), 1.71 (m, 2H), 3.60 (d, 2H), 3.62 (m, 1H), 6.08(d, 1H), 6.30 (d, 1H), 7.34 (s, H), 7.41 (d, 2H), 7.70 (d, 2H); ESIMS: m/z 396 (M+H).

Example 10

Preparation of methyl-3-{4-[2,2,2-trifluoro-1-hydroxy-1-(trifluoromethyl)ethyl]phenyl}-4,5-dihydroisoxazole-5-carboxylate

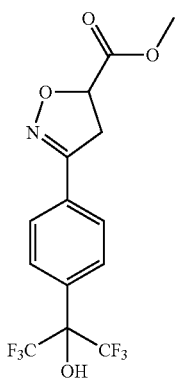

Step 1

DIBAL (12 mL, 1 M in Toluene) is added dropwise to a solution of the Weinreb amide (1.66 g, 5 mmol, Example 6, Step 2) in THF (15 mL) at −78° C. under argon atmosphere. The reaction mixture is stirred at the temperature for 2 hours. The reaction mixture is poured into 1N HCl and extracted with EtOAc three times. The combined organic solvent is washed with saturated NaHCO₃, brine and dried over MgSO₄. The organic solvent is removed under reduced pressure to afford the benzaldehyde intermediate as colorless solid (1.27 g).

Step 2

The benzaldehyde intermediate (1.0 g) and hydroxyamine hydrochloric acid (1.27 g) are mixed in MeOH (8 mL). The reaction mixture is stirred at room temperature for 12 hours. The solvent is removed under reduced pressure and the residue is partitioned between EtOAc and water. The aqueous layer is extracted with EtOAc. The combined organic solvent is washed with brine and dried MgSO₄. Removal of solvent affords the oxime intermediate (1.1 g).

Step 3

NBS (208 mg) is added to a solution of oxime intermediate (225 mg) obtained above in DMF (1 mL) at room temperature. After stirring for 1 hour, methyl acrylate (0.14 mL) is added followed by Et₃N (0.22 mL). The reaction mixture is stirred for 12 hours and diluted with EtOAc. The organic layer is washed with 1N HCl, saturated NaHCO₃, brine and dried over MgSO₄. The residue after removal of the solvent is purified by preparative TLC (CH₂Cl₂:MECN, 95:5) to afford the title compound (119 mg). ¹H NMR δ3.62 (dd, 2H), 3.80 (s, 3H), 4.48 (bs, 1H), 5.20 (dd, 1H), 7.75 (m, 4H); ESIMS: m/z 370 (M−H).

Example 11

Preparation of 3-{4-[2,2,2-Trifluoro-1-hydroxy-1-(trifluoromethyl)ethyl]phenyl}-4,5-dihydro-isoxazole-5carboxylic acid

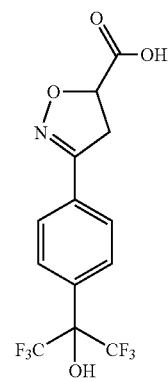

To a solution of methyl ester (90 mg, 0.24 mmol) prepared in the above example in methanol was added NaOH aq. (1.0 M, 0.2 ml) at room temperature. The mixture was then heated reflux for 3 hrs and poured into water. The solution was extracted with ethyl acetate and the organic layer was washed with brine and dried over MgSO₄. The solvent was evaporated off and the residue was subjected to preparative TLC (AcOEt:methanol=10:1) to give the title compound (55 mg, 63%). ¹H NMR δ 3.51 (dd, 1H), 3.64 (dd, 1H), 5.00 (dd, 1H), 7.98 (s, 4H).

Example 12

Preparation of 1,1-dimethylethyl N-[(3-{4-[2,2,2-trifluoro-1-hydroxy-1-(trifluoromethyl)ethyl]phenyl}-4,5-dihydroisoxazol-5-yl)carbonyl]-beta-alaninate

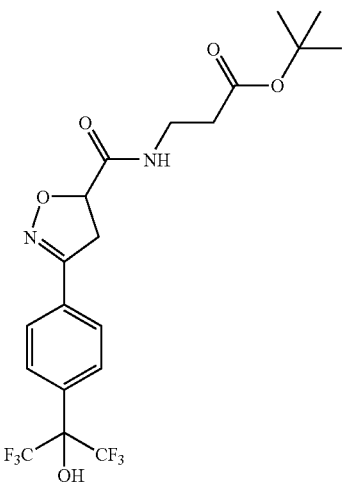

To a solution of the acid (18 mg, 0.05 mmol) in DMF (1 ml) prepared in the above example were added H-beta-Ala-OtBu HCl salt (11 mg, 0.75 mmol), BOP (44 mg, 0.1 mmol) and N-methyl morpholine (20 mg, 0.2 mmol) at room temperature. The reaction mixture was stirred for 12 hrs and then, water was added. The solution was extracted with ethyl acetate. The organic layer was washed with brine and dried over $MgSO_4$. The solvent was evaporated off and the residue was subjected to preparative TLC (Hexane:AcOEt=2:1) to give the title compound (15 mg, 61%). $^1$H NMR δ 1.39 (s, 9H), 2.45 (m, 2H), 3.35-3.51 (m, 2H), 3.60 (dd, 1H), 3.75 (dd, 1H), 5.15 (dd, 1H), 7.80 (s, 4H); ESIMS: m/z 483 (M–H).

Example 13

Preparation of ethyl 5-methyl-3-{4-[2,2,2-trifluoro-1-hydroxy-1-(trifluoromethyl)ethyl]phenyl}isoxazole-4-carboxylate

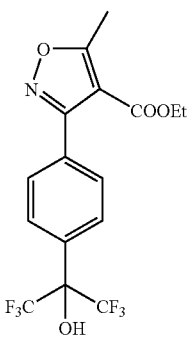

To a solution of oxime intermediate (50 mg, 0.17 mmol, cf. Example 10, Step 2) in DMF (1.5 ml) was added NBS (46 mg, 0.26 mmol) at 0° C. and the mixture was stirred for 3 hrs. To the solution were added ethyl acetoacetate (34 mg, 0.26 mmol) and sodium ethoxide ethanol solution (80 mg, 0.26 mmol) at room temperature. The reaction mixture was stirred for 12 hrs and diluted with ethyl acetate. The organic layer was washed with water and brine and dried over MgSO4. The solvent was evaporated off and the residue was purified by preparative TLC (CHCl$_3$:MeOH=50:1) to give the title compound (18 mg, 26%). $^1$H NMR δ 1.09 (t, 3H), 2.75 (s, 3H), 3.75 (b, 1H), 4.21 (q, 2H), 7.70 (d, 2H), 7.79 (d, 2H); ESIMS: m/z 396 (M–H).

Example 14

TABLE 3

The following compounds are prepared in accordance with the procedure described in the above examples.

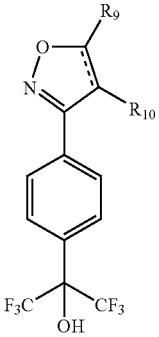

| Example | R$_9$ | R$_{10}$ |
|---|---|---|
| Example 14-1 | —COOEt | —H |
| Example 14-2 | -Me | —COOEt |
| Example 14-3 | -Ph | —COOEt |
| Example 14-4 | 2-Pyridinyl | —COOEt |
| Example 14-5 | 3-Pyridinyl | —COOEt |
| Example 14-6 | 4-Pyridinyl | —COOEt |
| Example 14-7 | MeOCH$_2$— | —COOEt |
| Example 14-8 | CF$_3$— | —COOMe |
| Example 14-9 | NH$_2$— | —CN |
| Example 14-10 | MeCONH— | —CN |
| Example 14-11 | 4-Pyridinyl- | —SO$_2$Me |
| Example 14-12 | H— | —H |
| Example 14-13 | —CONHCH$_2$CH$_2$COO(t-Bu) | —H |
| Example 14-14 | —CONHBn | -Me |
| Example 14-15 | —CONH(n-Pr) | —COOH |
| Example 14-16 | —CONH(n-Bu) | —H |
| Example 14-16 | —CONHCH$_2$(4-Py) | —COOH |
| Example 14-17 | —CONHCH$_2$(4-Py) | —CH$_2$OH |

Example 15

Preparation of 3-{4-[2,2,2-trifluoro-1-hydroxy-1-(trifluoromethyl)ethyl]phenyl}heptan-3-ol

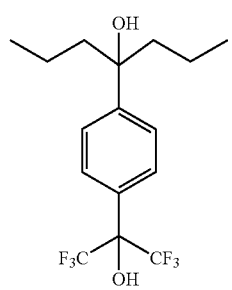

Propylmagnesium bromide (1 mL) is added to the solution of 1-(4-{2,2,2-trifluoro-1-hydroxy-1-trifluoromethyl)phenyl}-butan-1-one (170 mg, Example 6) in THF (2 mL) at 0° C. under argon atmosphere. The reaction mixture is stirred at room temperature for 12 hours and poured into ice cold 1N HCl and extracted with EtOAc three times. The combined organic solvent is washed with saturated NaHCO$_3$, brine and dried over MgSO$_4$. The residue after removal of the solvent is purified by preparative TLC to afford the title compound (99.4mg). $^1$H NMR δ0.82 (t, 6H), 1.02 (m, 2H), 1.25 (m, 2H), 1.80 (m, 4H), 3.41 (s, 1H), 7.42 (d, 2H) 7,62 (d, 2H). ESIMS: m/z 357 (M–H).

Example 16

Preparation of 2-[4-(3,5-Dimethyl-isoxazol-4-yl)-phenyl]-1,1,1,3,3,3-hexafluoro-propan-2-ol

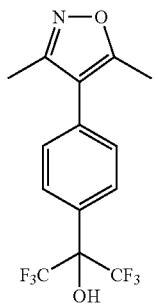

Step 1

2-(4-bromophenyl)-1,1,1,3,3,3-hexafluoropropan-2-ol (723 mg, 2.24 mmol), bis(pinacolato) diborane (625 mg, 2.46 mmol) and KOAc (659 mg, 6.72 mmol) are mixed in DMF (15 mL). The suspension is deoxygenated by nitrogen flow before Pd(dppf)Cl$_2$ (60 mg) is added. After been heated at 90° C. for 30 mins under nitrogen atmosphere, the reaction mixture is partitioned between EtOAc and water. The organic layer is dried over Na$_2$SO$_4$ and condensed under reduced pressure. The residue is subjected to flash column chromatography (Hexane:EtOAc, 5:1) to afford the arylboronate intermediate as white solid (650 mg, 78%). $^1$H NMR (CDCl$_3$) δ 1.33 (s, 1H), 3.88 (s, 1H), 7.70 (d, 2H), 7.87 (d, 2H); ESIMS: m/z 369.9 (M).

Step 2

The arylboronate intermediate (50 mg, 0.135 mmol), 4-bromo-3,5-dimethyl isoxazole (33 mg, 0.189 mmol) and saturated NaHCO$_3$ solution (2 mL) are mixed in THF (5 mL). The suspension is deoxygenated by nitrogen flow before Pd(dppf)Cl$_2$ (10 mg) is added. After been heated at 70° C. for 7 hrs under nitrogen atmosphere, the reaction mixture is partitioned between EtOAc and water. The organic layer is dried over Na$_2$SO$_4$ and condensed under reduced pressure. The residue is subjected to flash column chromatography (Hexane:Acetone, 5:1) to afford the title compound as white solid (18 mg, 39%). $^1$H NMR (CD$_3$OD) δ 2.27 (s, 3H), 2.42 (s, 3H), 7.45 (d, 2H), 7.82 (d, 2H); ESIMS: m/z 337.8 (M–H).

Example 17

Preparation of N-(5-methyl-4-{4-[2,2,2-trifluoro-1-hydroxy-1-(trifluoromethyl)ethyl]phenyl}isoxazol-3-yl)-N'-phenylurea

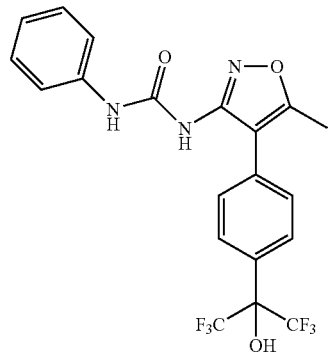

Step 1

1,1-Dimethylethyl 5-methyl-4-{4-[2,2,2-trifluoro-1-hydroxy-1-(trifluoromethyl)ethyl]phenyl}isoxazol-3-ylcarbamate (40 mg, 0.09 mmol) prepared according to the above example, is treated with 50% TFA in CH$_2$Cl$_2$ (2 mL) at room temperature. The reaction mixture is stirred for another 1 h and condensed under reduced pressure. The residue is purified by preparative TLC (Hexane:Acetone, 1:1) to afford the amine intermediate as white solid (24 mg, 78%). $^1$HNMR (CD$_3$OD) δ 2.32 (s, 3H), 7.49 (d, 2H), 7.82 (d, 2H); ESIMS: m/z 338.9 (M–H).

Step 2

The solution of the amine intermediate (45 mg, 0.13 mmol) and phenyl isocyanate (34 μL, 0.5 mmol) in pyridine (2 mL) is stirred at 90° C. under nitrogen atmosphere for 4 hrs. The reaction mixture is diluted with EtOAc, washed with saturated CuSO$_4$ solution and brine, dried over Na$_2$SO$_4$ and condensed under reduced pressure. The residue is purified by preparative TLC (CH$_2$Cl$_2$:Methanol, 20:1) to afford the title compound as white solid (38 mg, 63%). $^1$H NMR (CD$_3$OD) δ 2.38 (s, 3H), 7.02 (t, 1H), 7.25 (t, 2H), 7.38 (d, 2H), 7.50 (d, 2H), 7.86 (d, 2H); ESIMS: m/z 457.9 (M–H).

Example 18

Preparation of ethyl (2E)-3-(5-methyl-4-{4-[2,2,2-trifluoro-1-hydroxy-1-(trifluoromethyl)ethyl]phenyl}isoxazol-3-yl)prop-2-enoate

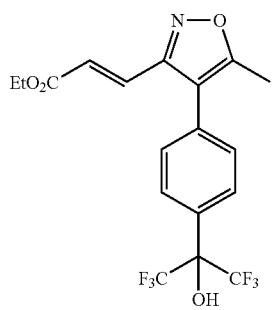

51

Step 1

Ethyl 5-methyl-4-{4-[2,2,2-trifluoro-1-hydroxy-1-(trifluoromethyl)ethyl]phenyl}isoxazole-3-carboxylate (1.9 g, 4.78 mmol) prepared according to example 16 is dissolved in methanol (20 mL) and treated with the solution of NaOH (1.0 g, 23.9 mmol) in water (10 mL) at room temperature. The reaction mixture is stirred for another 1 h, then diluted with water and extracted with EtOAc. The aqueous phase was acidified with 1 N HCl solution to PH 2 and extracted with EtOAc. The organic layer is dried over $Na_2SO_4$. Removal of the solvent under reduced pressure affords the acid intermediate as white solid (1.56 g, 89%.). $^1$HNMR ($CD_3OD$) δ 2.44 (s, 3H), 4.91 (s, 1H), 7.45 (d, 2H), 7.77 (d, 2H); ESIMS: m/z 324.0 (M–COOH).

Step 2

To the solution of the acid intermediate (150 mg, 0.406 mmol) in THF (2 mL) is added 1 M solution of oxalyl chloride in $CH_2Cl_2$ (812 μL) under nitrogen atmosphere, and followed by 4 drops of DMF. The reaction mixture is stirred at room temperature for 1 h. After removal of the solvent under reduced pressure, the residue is dissolved in THF (1 mL) and added the solution of N, O-dimethylhydroxylamine hydrochloride (80 mg, 0.812 mmol) and triethyl amine (113 μL, 0.812 mmol) in THF (1 mL). The reaction mixture is stirred at room temperature for 2 hrs before being quenched with 1 N HCl solution. EtOAc is used to extract, and the organic layer is washed with 1 N HCl, sat. $NaHCO_3$ and brine, then dried over $Na_2SO_4$. After removal of solvent under reduced pressure, the residue is purified by preparative TLC (hexane:EtOAc, 3:1) to afford the Weinreb amide intermediate as white solid (45 mg, 27%). $^1$HNMR ($CDCl_3$) δ 2.48 (s, 3H), 3.22 (s, 3H), 3.57 (s, 3H), 4.69 (b, 1H), 7.33 (d, 2H), 7.68 (d, 2H); ESIMS: m/z 413.0 (M+H).

Step 3

The suspension of $LiALH_4$ (14 mg, 0.335 mmol) in THF (0.5 mL) is charged with the solution of the Weinreb amide intermediate in THF (1 mL) at –40° C. under nitrogen atmosphere. The cooling bath is removed after the addition and the reaction mixture is allowed to warm up to room temperature in 2 hrs. After quenching with 0.1 N HCl solution, the suspension is extracted with EtOAc, washed with 1 N HCl solution, saturated $NaHCO_3$ solution and brine, then dried over $Na_2SO_4$. After removal of solvent under reduced pressure, the residue is purified by preparative TLC (hexane:EtOAc, 2:1) to afford the aldehyde intermediate as yellow oil (33 mg, 56%). $^1$HNMR ($CDCl_3$) δ 2.51 (s, 3H), 4.61 (b, 1H), 7.41 (d, 2H), 7.78 (d, 2H), 10.17 (s, 1H); ESIMS: m/z 324.0 (M–CHO).

Step 4

The aldehyde intermediate (13 mg, 0.037 mmol) and (carbethoxy methylene)triphenylphosphorane (14 mg, 0.04 mmol) are mixed in toluene (1 mL). The reaction mixture is stirred at 90° C. for 3 hrs before condensed under reduced pressure. The residue is purified by preparative TLC (hexane:Acetone, 2:1) to afford the title compound as white solid (13 mg, 81%). $^1$HNMR ($CD_3OD$) δ 1.17 (t, 3H), 2.36 (s, 3H), 4.11 (q, 2H), 6.36 (d, 1H), 7.34 (d, 2H), 7.37 (d, 2H), 7.79 (d, 2H); ESIMS: m/z 421.8 (M–H).

52

Example 19

Preparation of N-{3-Phenyl-4-[4-(2,2,2-trifluoro-1-hydroxy-1-trifluoromethyl-ethyl)-phenyl]-isoxazol-5-yl}-isobutyramide

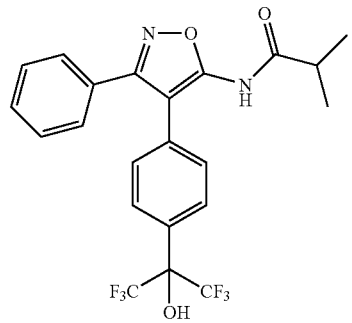

Step 1

1 M of LHDMS in THF (10.6 ml 10.6 mmol) is added to the solution of 4-hexafluoro-2-hydroxyisopropyl phenyl acetonitrile in THF at room temperature under argon atmosphere. The reaction mixture is stirred at room temperature under argon atmosphere for 30 minutes before adding methyl benzoate (527 μl 4.24 mmol). Then the solution is allowed to stir for 8 hours. $H_2O$ is poured to the reaction mixture, and the solution is washed with EtOAc. The aqueous layer is acidified by 1N HCl and extracted with EtOAc. This organic layer is then washed with brine and dried over $MgSO_4$. Concentration and purification by preparative TLC afford the intermediate 3-Oxo-2-[4-(2,2,2-trifluoro-1-hydroxy-1-trifluoromethyl-ethyl)-phenyl]-butyronitrile.

Step 2

The above intermediate (560.8 mg 1.45 mmol) and hydroxyamine hydrochloric acid (20 mg 2.9 mmol) are mixed in 2.5 ml pyridine. The reaction mixture is stirred at 80° C. for 12 hours. The reaction mixture is diluted with EtOAc and washed with Sat. $NaHCO_3$, $H_2O$ and brine and dried over $MgSO_4$. Concentration and purification by preparative TLC afford the 2-[4-(5-Amino-3-phenyl-isoxazol-4-yl)-phenyl]-1,1,1,3,3,3-hexafluoro-propan-2-ol (260 mg 45%).

Step 3

Sodium hydride (18 mg 0.45 mmol) is added to the solution of 2-[4-(5-Amino-3-phenyl-isoxazol4-yl)-phenyl]-1,1,1,3,3,3-hexafluoro-propan-2-ol in DMF at 0° C. under argon atmosphere. The reaction mixture is stirred at room temperature under argon atmosphere for 30 minutes before adding isobutyryl chloride (23.8 ul, 0.23 mmol). The solution is allowed to stir for 8 hours and diluted with EtOAc. The organic layer is washed with $H_2O$ brine and dried over $MgSO_4$. Concentration and purification by preparative TLC afford the title compound. $^1$HNMR 1.11 (s, 3H), 1.12 (s, 3H), 2.60 (m, 1H), 7.26 (d, 2H), 7.4 (m, 5H), 7.72 (d, 2H); ESIMS: m/z 471 (M–H).

Example 20

TABLE 4

The following compounds are prepared in accordance with the procedure described in the above example

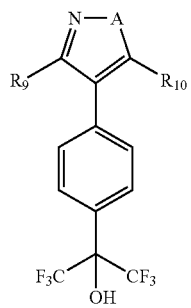

| Example | R<sub>9</sub> | R<sub>10</sub> | A |
|---|---|---|---|
| Example 20-1 | 4-Pyr- | $NH_2$— | O |
| Example 20-2 | Ph- | $NH_2$— | O |
| Example 20-3 | Et- | $NH_2$— | O |
| Example 20-4 | Bu- | $NH_2$— | O |
| Example 20-5 | EtOCH$_2$— | $NH_2$— | O |
| Example 20-6 | 4-MeOPh- | $NH_2$— | O |
| Example 20-7 | i-Pr- | $NH_2$— | O |
| Example 20-8 | Ph- | i-PrCONH— | O |
| Example 20-9 | 4-Pyr- | i-PrCONH— | O |
| Example 20-10 | Ph- | i-PrNHCONH— | O |
| Example 20-11 | HOOCCH$_2$CH$_2$— | $NH_2$— | O |
| Example 20-12 | 4-HOPh- | $NH_2$— | O |
| Example 20-13 | Bn- | $NH_2$— | O |
| Example 20-14 | HOCH$_2$CH$_2$CH$_2$— | $NH_2$— | O |
| Example 20-15 | CF$_3$— | $NH_2$— | O |
| Example 20-16 | MeCHCHCH$_2$— | $NH_2$ | O |
| Example 20-17 | 3-Pyr- | $NH_2$ | O |
| Example 20-18 | Furyl- | $NH_2$ | O |
| Example 20-19 | 3-Indolylmethyl- | $NH_2$ | O |
| Example 20-20 | Ph- | $NH_2$ | NH |
| Example 20-21 | Me- | Me | O |
| Example 20-22 | t-BuOCONH— | Me | O |
| Example 20-23 | MeCONH— | Me | O |
| Example 20-24 | $NH_3^+$ | Me | O |
| Example 20-25 | EtOCOCH$_2$NHCONH— | Me | O |
| Example 20-26 | PhNHCONH— | Me | O |
| Example 20-27 | (i-BuOCO)$_2$N— | Me | O |
| Example 20-28 | HOOCCH$_2$NHCONH— | Me | O |
| Example 20-29 | Cyclohexyl- | Me | O |
| Example 20-30 | EtOCOCH[CH$_2$CH(Me)$_2$]NHCONH— | Me | O |
| Example 20-31 | HOOCOCH[CH$_2$CH(Me)$_2$]NHCONH— | Me | O |
| Example 20-32 | EtOCO— | Me | O |
| Example 20-33 | EtOCOCH(CH$_2$CH$_2$SMe)NHCONH— | Me | O |
| Example 20-34 | PhCH$_2$CH$_2$NHCONH$_2$— | Me | O |
| Example 20-35 | HOOCOCH(CH$_2$CH$_2$SMe)NHCONH— | Me | O |
| Example 20-36 | 4-(3,,5-dimethyl)-isoxazolyl- | Me | O |
| Example 20-37 | HOOC— | Me | O |
| Example 20-38 | 4-CF$_3$PhSO$_2$NH— | Me | O |
| Example 20-39 | HOCH$_2$— | Me | O |
| Example 20-40 | 5-(4-Me-2-MeCONH)-thiazolyl- | Me | O |
| Example 20-41 | (Me)$_2$NCO— | Me | O |
| Example 20-42 | PhCH$_2$CH$_2$CONH— | Me | O |
| Example 20-43 | (Me)$_2$CHCONH— | Me | O |
| Example 20-44 | (MeO)NMeCO— | Me | O |
| Example 20-45 | 4-PyCO— | Me | O |
| Example 20-46 | MeCH$_2$CH$_2$CH$_2$CH$_2$CONH— | Me | O |
| Example 20-47 | NCCH=CH— | Me | O |
| Example 20-48 | MeCH$_2$CH$_2$CO | Me | O |
| Example 20-49 | EtOCOCH=CH | Me | O |

Example 22

Preparation of N-butyl-4-phenyl-1-propyl-2-{4-[2,2,2-trifluoro-1-hydroxy-1-(trifluoromethyl)ethyl]phenyl}-1H-imidazole-5-carboxamide

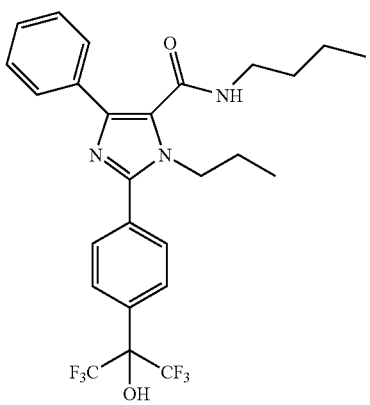

Step 1

To a solution of 4-(2-Hydorxy-hexafluoroisopropyl)-benzoic acid (100 mg, 0.35 mmol) and phenylglyoxal hydrate (46 mg, 0.35 mmol) in methanol (1.5 ml) was added propylamine (20 mg, 0.35 mmol) at room temperature. After being stirred for 5 mins, butyl isocyanide (83 mg, 0.35 mmol) was added to the mixture at room temperature. The resultant mixture was stirred for 12 hrs at the same temperature and acidified with 0.1N HCl solution. The mixture was extracted with ethyl acetate and the organic layer was washed with water and brine and dried over $MgSO_4$. The solvent was evaporated off under reduced pressure. The residue (165 mg) was used for the next step without further purification.

Step 2

The residue obtained (54 mg) was dissolved in acetic acid (1 ml) and ammonium acetate (77 mg, 1 mmol) was added. The reaction mixture was stirred under reflux condition for 3 hrs. After being diluted with water, the mixture was extracted with ethyl acetate. The organic layer was washed with brine and dried over MgSO4. The solvent was evaporated off under reduced pressure. The residue was purified by preparative TLC (Hexane:EtOAc, 2:1) to afford the title compound (24 mg, 46%). $^1$H NMR δ 0.79 (t, 3H), 0.83 (t, 3H), 1.09 (m, 2H), 1.34 (m, 2H), 1.70 (m, 2H), 3.28 (m, 2H), 4.28 (m, 2H), 5.72 (t, 1H), 6.34 (b, 1H), 7.35-7.47 (m, 3H), 7.55 (d, 2H), 7.62 (d, 2H), 7.75 (m, 2H); ESIMS: m/z 528 (M+H).

Example 23

TABLE 5

The following compounds are prepared in accordance with the procedure described in the above examples.

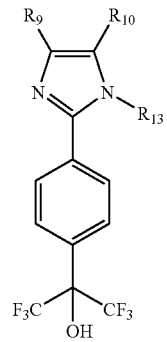

| Example | $R_9$ | $R_{10}$ | $R_{13}$ |
|---|---|---|---|
| Example 23-1 | Ph- | H— | n-Pr- |
| Example 23-2 | $HOCH_2$— | H— | H— |
| Example 23-3 | Me- | H— | H— |
| Example 23-4 | i-PrCOOCH$_2$— | H— | H— |
| Example 23-5 | 2-Pyridinyl- | 2-Pyridinyl- | n-Pr- |
| Example 23-5 | 2-Pyridinyl- | H— | H— |
| Example 23-6 | Ph- | n-BuNHCO— | n-Pr- |
| Example 23-7 | Ph- | n-BuNHCO— | 2-Pyridinylmethyl- |
| Example 23-8 | Ph- | n-BuNHCO— | 1-morpholinyl-CH$_2$CH$_2$— |
| Example 23-9 | Ph- | n-BuNHCO— | CNCH$_2$CH$_2$— |
| Example 23-10 | Ph- | n-BuNHCO— | HOCH$_2$CH$_2$CH$_2$— |
| Example 23-11 | Ph- | n-BuNHCO— | i-Pr- |
| Example 23-12 | Ph- | MeO$_2$CCH$_2$NCO— | n-Pr- |
| Example 23-13 | Ph- | HOOCCH$_2$NCO— | n-Pr- |
| Example 23-14 | Ph- | n-BuNHCO— | i-Bu- |
| Example 23-15 | 2-Pyridinyl- | n-BuNHCO— | n-Pr- |
| Example 23-16 | 3-Pyridinyl- | n-BuNHCO— | i-Bu- |
| Example 23-17 | 4-Pyridinyl- | n-BuNHCO— | i-Bu- |
| Example 23-18 | 4-Pyridinyl- | n-BuNHCO— | CNCH$_2$CH$_2$— |
| Example 23-19 | MeSO$_2$NHCH$_2$— | H— | H— |

TABLE 5-continued

The following compounds are prepared in accordance with the procedure described in the above examples.

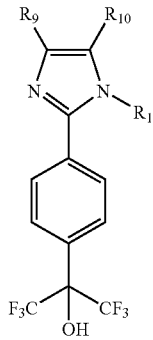

| Example | $R_9$ | $R_{10}$ | $R_{13}$ |
|---|---|---|---|
| Example 23-20 | p-CN-Ph- | n-BuNHCO— | n-Bu- |
| Example 23-21 | 2-Me-isoxazolyl- | —COOH | 4-Pyridinylmethyl- |
| Example 23-22 | Ph- | —CONHi-Bu | i-Bu- |
| Example 23-23 | Ph- | —CONHi-Bu | 2-Pyridinylmethyl- |
| Example 23-24 | Ph- | —CONHCH$_2$CH$_2$COOH | 2-Pyridinylmethyl- |
| Example 23-25 | Ph- | CON(iBu)$_2$— | 2-Pyridinylmethyl- |
| Example 23-26 | 2-Furyl- | —CONHi-Bu- | 2-Pyridinylmethyl- |
| Example 23-27 | —COOH | H— | i-Bu- |
| Example 23-28 | CONH-i-Bu | CONHBu- | 2-Pyridinylmethyl- |

Example 24

Preparation of 1-Methyl-3-{4-[2,2,2-trifluoro-1-(trifluoromethyl)ethyl]phenyl}-1H-pyrazole-4-carbonitrile.

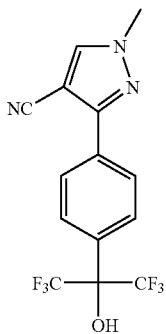

Step 1

To a solution of 4-[2,2,2-trifluoro-1-hydroxy-1-(trifluoromethyl)ethyl]benzaldehyde (200 mg, 0.735 mmol) in benzene (1.5 mL) is added a solution of methylhydrazine (51 mg, 1.1 mmol) in benzene (1 mL) at room temperature under nitrogen. The mixture is stirred under reflux conditions for 2 h. The mixture is allowed to cool to room temperature and then dried over MgSO$_4$. The solvent is removed under reduced pressure to afford the product methyl hydrazone (145 mg, 66%) which is used in the next step without purification. $^1$H NMR (CDCl$_3$) δ 2.96 (s, 3H), 3.79 (b, 1H), 7.47 (s, 1H), 7.58 (d, 2H), 7.67 (d, 2H).

Step 2

Dimethyl sulfide (90 mg, 1.45 mmol) is added to a solution of N-chlorosuccinimide (107 mg, 0.805 mmol) in CH$_2$Cl$_2$ (5.5 mL) at 0° C. The mixture is stirred at 0° C. for 5 minutes, then cooled to −70° C. To the solution is added dropwise a solution of methyl hydrazone (145 mg, 0.483 mmol) from above in CH$_2$Cl$_2$ (1 mL). The mixture is stirred for 4.5 h, gradually allowing the temperature to warm to 0° C. The reaction is quenched with cold water and extracted with CH$_2$Cl$_2$. The organic layer is washed with water and brine, then dried over MgSO$_4$. The solvent is removed under reduced pressure to afford the hydrazonoyl chloride intermediate (115 mg, 71%) which is used in the next step without purification. $^1$HNMR (CDCl$_3$) δ 3.18 (s, 3H), 7.69 (d, 2H), 7.75 (s, 1H), 7.86 (d, 2H).

Step 3

To a solution of hydrazonoyl chloride intermediate (115 mg, 0.344 mmol) from above in CHCl$_3$ (3 mL) is added fumaronitrile (27 mg, 0.344 mmol), followed by Et$_3$N (35 mg, 0.344 mmol) at room temperature. The mixture is stirred under reflux conditions overnight. After cooling to r.t., the reaction is diluted with CHCl$_3$, washed with water, and dried over MgSO$_4$. The solvent is removed under reduced pressure and the residue is purified by preparative TLC (Hexane: EtOAc, 3:1) to afford the title compound as a light yellow solid (25 mg, 21%). $^1$H NMR (DMSO) δ 3.93 (s, 3H), 7.80 (d, 2H), 7.95 (d, 2H), 8.62 (s, 1H), 8.83 (b, 1H); ESIMS: m/z 348 (M−H).

Example 25

Preparation of N,N-1-trimethyl-3-{4-[2,2,2-trifluoro-1-hydroxy-1-(trifluoromethyl)ethyl]phenyl}-4,5-dihydro-1H-pyrazole-5-carboxamide.

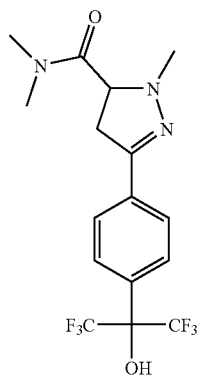

Step 1

To a mixture of hydrazonoyl chloride intermediate (204 mg, 0.610 mmol) (as obtained in Step 2 of Example 24 above) and N,N-dimethylacrylamide (61 mg, 0.610 mmol) in $CHCl_3$ is added $Et_3N$ (62 mg, 0.610 mmol). The reaction mixture is stirred at room temperature for 5 days. The solvent is removed under reduced pressure, and the residue is dissolved in EtOAc, washed with water, and dried over $MgSO_4$. The solvent is removed under reduced pressure and the residue is purified by preparative TLC (hexane:EtOAc, 2:1) to afford the title compound as a white solid (29 mg, 12%). $^1$HNMR (DMSO-$d_6$) δ 2.83 (s, 3H), 2.85 (s, 3H), 2.99 (dd, 1H), 3.04 (s, 3H), 3.45 (dd, 1H), 4.28 (t, 1H), 7.65 (m, 4H), 8.71 (s, 1H); ESIMS: m/z 396 (M–H).

Example 26

Preparation of N,N-bis(1-methylethyl)-N'-phenyl-4-[2,2,2-trifluoro-1-hydroxy-1-(trifluoro-methyl)ethyl]benzenecarbohydrazonamide.

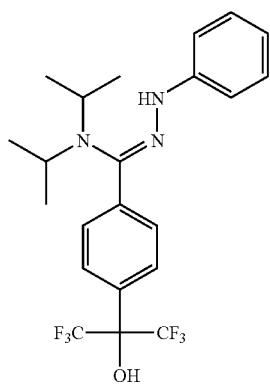

Step 1

To a solution of 4-[2,2,2-trifluoro-1-hydroxy-1-(trifluoromethyl)ethyl]benzaldehyde (500 mg, 1.84 mmol) in benzene (3 mL) is added phenylhydrazine (200 mg, 1.84 mmol) at room temperature. The mixture is stirred at r.t. for 4 h. The solvent is removed under reduced pressure to afford the product phenyl hydrazone (656 mg, 99%) which is used in the next step without purification. $^1$H NMR ($CDCl_3$) δ 3.62 (b, 1H), 6.88 (t, 1H), 7.10 (d, 2H), 7.28 (t, 2H), 7.34 (s, 1H), 7.70 (m, 4H).

Step 2

Dimethyl sulfide (338 mg, 5.43 mmol) is added to a solution of N-chlorosuccinimide (404 mg, 3.02 mmol) in $CH_2Cl_2$ (21 mL) at 0° C. The mixture is stirred at 0° C. for 5 minutes, then cooled to –70° C. To the solution is added dropwise a solution of phenyl hydrazone (656 mg, 1.81 mmol) from above in $CH_2Cl_2$ (3 mL). The mixture is stirred for 2 h, gradually allowing the temperature to warm to 0° C. The reaction is quenched with cold water and extracted with $CH_2Cl_2$. The organic layer is washed with water and brine, then dried over $MgSO_4$. The solvent is removed under reduced pressure to afford the hydrazonoyl chloride intermediate (387 mg, 54%) which is used in the next step without purification. $^1$H NMR ($CDCl_3$) δ 3.60 (b, 1H), 6.88 (t, 1H), 7.17 (d, 2H), 7.32 (t, 2H), 7.74 (d, 2H), 8.00 (d, 2H), 8.10 (s, 1H); ESIMS: m/z 395 (M–H).

Step 3

A solution of hydrazonoyl chloride intermediate (100 mg, 0.252 mmol) in 1,4-dioxane (1.5 mL) is added dropwise to diisopropylamine (7.5 mL) at 0° C. over a period of 26 h. The mixture is stirred at room temperature for an additional 3.5 h. Solvents are removed under reduced pressure, and the residue is dissolved in EtOAc, washed with water and brine, and dried over $MgSO_4$. Solvent is removed under reduced pressure, and the residue is purified by preparative HPLC to afford the title compound as a light yellow solid (26 mg, 22%). $^1$H NMR (DMSO) δ 1.17 (d, 7H), 1.55 (d, 5H), 3.52 (m, 1.2H), 4.29 (m, 0.8H), 6.73 (d, 2H), 6.80 (t, 1H), 7.16 (t, 2H), 7.68 (d, 2H), 7.76 (d, 2H), 8.28 (b, 1H), 8.91 (b, 1H); ESIMS: m/z 462 (M+H).

Example 27

Preparation of diethyl 4-[2,2,2-trifluoro-1-hydroxyl-1-(trifluoromethyl)ethyl]phenyl amido phosphate

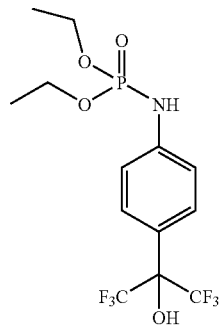

To a solution of 2-(4-aminophenyl)-1,1,1,3,3,3)-hexafluoroisopropan-2-ol (777.4 mg, 3 mmol), DMAP (146.4 mg, 1.2 mmol), $Et_3N$ (0.5 ml, 3.6 mmol) and $CH_2Cl_2$ (15 mL) was added diethyl chlorophoshate (520 mL, 3.3 mmol). The reaction mixture was stirred at room temperature for 72 hrs and then refluxed for another 24 hrs. The solvent was removed and EtOAc was added. The solution was washed with water. After removal of solvent, the residue was purified by a short Ion Exchange column (Dowex-50u, ethanol)) to afford the title compound as a whit solid (859 mg, 72.4%). $^1$HNMR (DMSO-$d_6$) δ1.20 (t, 6H), 3.89 (m, 4H), 7.08 (d, 2H), 7.46 (d, 2H), 8.24 (d, 2H), 8.43 (br, 1H); ESIMS: m/z 394 (M−H).

Example 28

Preparation of diethyl ethyl{4-[2,2,2-trifluoro-1-hydroxyl-1-(trifluoromethyl)ethyl]phenyl}amidophosphate

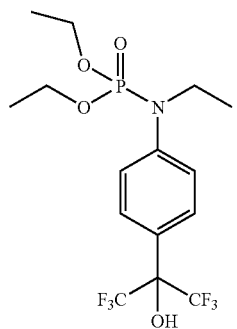

The compound was prepared in accordance with the procedure described in the above example. Yield: 8.5%; $^1$H NMR δ1.25 (d, t, 6H), 1.45 (t, 3H), 3.64-3.73 (m, 2H), 3.95-4.04 (m, 2H), 4.04-4.12 (m, 2H), 7.29 (d, 2H), 7.61 (d, 2H); ESIMS: m/z 422 (M−H).

Example 29

Preparation of diethyl 4-[2,2,2-trifluoro-1-hydro(trifluoromethyl)ethyl]phenyl phosphonate

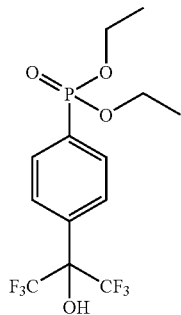

The mixture of 2-(4-bromophenyl)-1,1,1,3,3,3)-hexafluoroisopropan-2-ol (162 mg, 0.5 mmol), triethyl phosphite (154 μL, 0.9 mmol), anhydrous nickel chloride (13 mg, 0.1 mmol) and 3 ml diglyme was degassed for 15 minutes by argon. The reaction mixture was heated at 150° C. under argon for 5 hrs. After cooling, EtOAc was added and solution was washed with water, brine and dried over MgSO$_4$. The solvents were removed under reduced pressure and residue was purified by preparative TLC (MeOH:CHCl$_3$ 10:90) to afford the title compound as colorless oil (72.1 mg, 38%). $^1$HNMR δ1.31 (t, 6H), 4.10 (m, 4H), 5.90 (br, 1H), 7.69 (dd, 2H), 7.79 (dd, 2H); ESIMS: m/z 381 (M+H).

Example 30

Preparation of 2-phenoxy-N-[4-(trifluoroacetyl)phenyl]acetamide

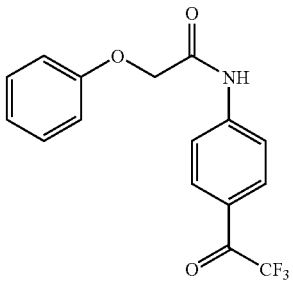

Step 1

Methyl 4-nitrobenzoate (4.0 g, 22.0 mmol) is dissolved in anhydrous CH$_2$Cl$_2$ (80 mL) under Argon atmosphere. The solution is then cooled to −78° C. (Trifluoromethyl) trimethylsilane (4.08 mL, 27.6 mmol) is added to the solution followed by solid tetrabutylammoniumfluoride (560 μL, 0.56 mmol). The light pink solution is then allowed to slowly warm to r.t. and stir for 20 h. The orange solution is washed with water, brine, dried over MgSO$_4$ and evaporated under reduced pressure. The crude TMS ether is then dissolved in acetone (60 mL) before adding 8 M HCl (30 mL) and trifluoroacetic acid (2 mL). The yellow solution is washed with water, saturated NaHCO$_3$, brine, dried over MgSO$_4$ and the solvent is evaporated under reduced pressure. The residue is purified by silica gel column chromatography (Hexane:CHCl$_3$, 1:9, CHCl$_3$, Methanol:CHCl$_3$, 3.5:96.5) to afford the title compound as yellow solid (3.05 g, 63.0%). $^1$H NMR δ7.78 (d, 2H), 8.20 (d, 2H); ESIMS: m/z 220 (M+H).

Step 2

4-Nitro-2',2',2',-trifluoroacetophenone (3.05 g, 13.9 mmol), glacial acetic acid (30 mL, 500 mmol), and Iron powder (4.7 g, 83 mmol) are added to 95% ethanol (63 mL). The mixture is then heated reflux for 17 h. The brown mixture is then filtered through Celite and evaporated under reduced pressure. The residue is co-evaporated twice with toluene to remove any remaining acetic acid. The brown solid is mixed with chloroform and filtered through a pad of silica gel to remove polar impurities, to afford the title compound as yellow solid (2.08 g, 79.1%). $^1$H NMR δ4.45 (bs, 2H), 6.67 (d, 2H) 7.90 (d, 2H); ESIMS: m/z 190 (M+H).

Step 3

4-Amino-2',2',2',-trifluoroacetophenone (595 mg, 3.15 mmol) and poly(4-vinylpyridine) (720 mg, 6.3 mmol) are mixed in anhydrous CH$_2$Cl$_2$ (20 mL). Phenoxyacetyl chloride (450 μL, 3.26 mmol) is added to the suspension and the reaction mixture is stirred at r.t. for 24 hrs. The mixture is filtered and the organic solvent is removed under reduced pressure. The yellow solid is purified by preparative TLC (100% CHCl$_3$) to afford the title compound as colorless solid (705 mg, 69.2%). $^1$H NMR δ4.62 (s, 2H), 6.97 (d, 2H), 7.07 (t, 1H), 7.34 (t, 2H), 7.79 (d, 2H), 8.06 (d, 2H), 8.59 (bs, 1H); ESIMS: m/z 324 (M+H).

Example 31

TABLE 6

The following compounds are prepared in accordance with the procedure described in the above example.

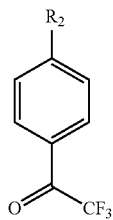

| Example | $R_2$ |
|---|---|
| Example 31-1 | PhOCH$_2$CONH— |
| Example 31-2 | PHOCH$_2$CON(Me)— |
| Example 31-3 | PhCH$_2$CH$_2$NHCO— |
| Example 31-4 | PhCH$_2$CH$_2$N(Me)— |
| Example 31-5 | PhN(iPr)CO— |
| Example 31-6 | p-CN-PhCONH— |
| Example 31-7 | iPrCONH— |
| Example 31-8 | 1-MorpholinylCONH— |
| Example 31-9 | iPrNHCO— |
| Example 31-10 | t-BuNHCO— |
| Example 31-11 | n-BuNHCO— |
| Example 31-12 | MeCH(Me)CH(Me)NHCO— |
| Example 31-13 | 2-FurylCH$_2$NHCO— |
| Example 31-14 | MeCH(Me)CH$_2$CH(Me)NHCO— |
| Example 31-15 | n-HexylNHCO— |
| Example 31-16 | 2-Methyl-c-HexylNHCO— |
| Example 31-17 | 2-Hepatyl-NHCO— |
| Example 31-18 | p-MeOPhNHCO— |
| Example 31-18 | p-NO$_2$PhNHCO— |
| Example 31-20 | m-CF$_3$PhCH$_2$NHCO— |
| Example 31-21 | 2-MeCO-4-thienyl-NHCO— |
| Example 31-22 | 3,5-bistrifluoromethylbenzylNHCO— |
| Example 31-23 | MeCH(OH)CH$_2$NHCO— |
| Example 31-24 | 1-Bn-piepradinyl-4-NHCO— |
| Example 31-25 | c-PrCH$_2$N(nPr)CO— |
| Example 31-26 | CNCH$_2$CH$_2$N(Ph)CO— |
| Example 31-27 | 1-PyrrolidinylCO— |
| Example 31-28 | i-Bu$_2$NCO— |
| Example 31-29 | 4-MeO$_2$CPhN(Me)CO— |
| Example 31-30 | MeC(OH)(Me)N(Et)CO— |
| Example 31-31 | CNCH$_2$CH$_2$N(Et)CO— |
| Example 31-32 | MeOCH$_2$CH$_2$N(Et)CO— |
| Example 31-33 | (4-ClBnCH(Me)N(c-PrCH$_2$)CO— |
| Example 31-34 | iPr$_2$N—CON(nPr)— |
| Example 31-35 | i-Pr$_2$NSO$_2$— |
| Example 31-36 | Et$_2$NCO— |
| Example 31-37 | n-Pr$_2$N— |
| Example 31-38 | nPr$_2$NCO— |
| Example 31-39 | 1-(2,6-dimethylpiperidinyl)CO— |
| Example 31-40 | t-BuCH$_2$CH$_2$NHCO— |
| Example 31-41 | n-Bu$_2$NCH$_2$CH$_2$CH$_2$NHCO— |
| Example 31-42 | Ph(CH$_2$)$_3$NHCO— |
| Example 31-43 | Ph(CH$_2$)$_4$NHCO— |
| Example 31-44 | c-Hex-CH$_2$NHCO— |
| Example 31-45 | 1-Morpholinyl-CH$_2$CH$_2$CH$_2$NHCO— |
| Example 31-46 | (Ph)$_2$CHCH$_2$NHCO— |
| Example 31-47 | (Ph)$_2$CHCH$_2$CH$_2$NHCO— |

All references described herein are hereby incorporated by reference, for example, all patents, patent applications cited are incorporated herein by reference.

Modification of the preceding embodiments is within the scope of the skilled artisan in formulation, given the guidance of the specification in light of the state of the art.

While particular embodiments of this invention have been described, it will be apparent to those skilled in the art that various changes and modifications of this invention can be made without departing from the spirit and scope of the invention. It is intended to cover, in the appended claims, all such modifications that are within the scope of this invention. Hence, the foregoing written specification is considered to be sufficient to enable one skilled in the art to practice the invention. Indeed, various modifications of the above-described makes for carrying out the invention which are obvious to those skilled in the fields of molecular biology, chemistry, medicine, pharmaceutics, or related fields are intended to be within the scope of the following claims.

We claim:

1. A compound of the following formula (Ia) or (Ib):

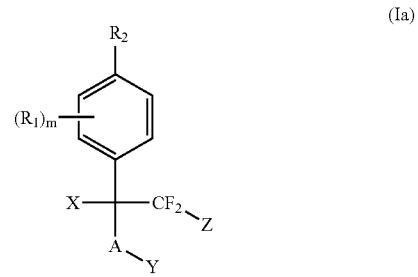

(Ia)

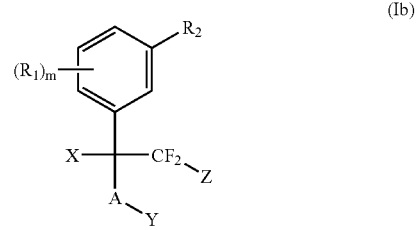

(Ib)

wherein $R_1$ is independently chosen from halo, haloalkyl, hydroxy, thiol, substituted thiol, sulfonyl, sulfinyl, nitro, cyano, amino, substituted amino, $C_1$-$C_6$ alkyl and $C_1$-$C_6$ alkoxy, and when $R_1$ is hydroxy, $C_1$-$C_6$ alkoxy, thiol, substituted thiol, amino, substituted amino, or $C_1$-$C_6$ alkyl, such radical may be combined with $R_2$ to form a ring of 5-7 members when $R_1$ is ortho to $R_2$;

$R_2$ is selected from $NR_3C(S)NR_4R_5$, $NR_3C(=NR_3)NR_4R_5$, $NR_3C(=NCN)NR_4R_5$, $NR_3C(=CHNO_2)NR_4R_5$, $NR_3P(O)R_4R_5$, $NR_3P(O)(OR_4)(OR_5)$, $NR_3P(O)(OR_4)(NR_5)$, $NR_3P(O)(NR_4)(NR_5)$, $NR_3C(=NR_3)R_6$, $COR_6$, $R_6C(OH)R_7$, $CR_8=NOR_4$, $CR_8=NR_3$, $CR_8=NNR_4R_5$, $SOR_7$, $SO_2R_7$, $P(O)(OR_4)(OR_5)$, $P(O)(R_4)(R_5)$, $P(O)(OR_4)(OR_5)$, $P(O)(NR_3)(OR_4)$, $P(O)(NR_4)(NR_5)$, a 3-7 membered ring containing from zero to three heteroatoms selected from O, N, or S, which may be substituted by $R_9$, $R_{10}$, $R_{11}$, $R_{12}$ or $R_{13}$, with the exception of the following groups:

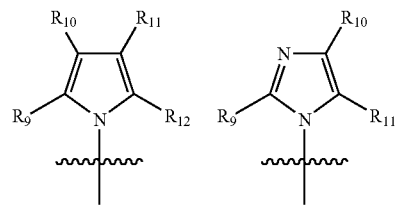

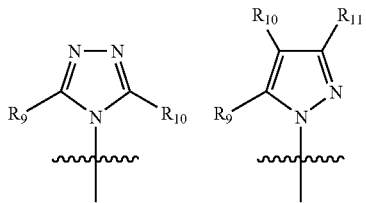

or may be combined with $R_1$ to form a ring of 5-7 members when $R_1$ is ortho to $R_2$;

$R_3$ is hydrogen, alkyl, aryl, heterocyclyl, acyl, or may form a ring of 5-7 members with $R_4$ or $R_5$;

$R_4$ is hydrogen, alkyl, aryl, heterocyclyl, acyl, or may form a ring of 5-7 members with $R_5$ or $R_3$;

$R_5$ is hydrogen, alkyl, aryl, or heterocyclyl, acyl or may form a ring of 5-7 members with $R_3$ or $R_4$;

$R_6$ and $R_7$ may be equal or different and are selected from hydrogen, alkyl, aryl, or heterocyclyl;

$R_8$ is hydrogen, alkyl, aryl, heterocyclyl, amino or substituted amino;

$R_9$, $R_{10}$, $R_{11}$ and $R_{12}$ may be equal or different and are selected from hydrogen, alkyl, aryl, heterocyclyl, nitro, cyano, carboxylic acid, ester, amide, halo, hydroxyl, amino, substituted amino, alkoxy, acyl, ureido, sulfonamido, sulfamido, sulfonyl, sulfinyl, or guanadinyl;

$R_{13}$ is hydrogen, alkyl, aryl, heterocyclyl, acyl, ester, sulfonyl, ureido, or guanadinyl;

A is O, S, or $NR_3$;

m is from zero to four;

X is H, $CF_2Z$, or $CF_3$, or together with Y forms a double bond when A is O;

Y is hydrogen, or together with X forms a double bond when A is O; and

Z is F, Br, Cl, I or $CF_3$;

its corresponding enantiomers, diastereoisomers or tautomers; or a pharmaceutically acceptable salt, or a prodrug thereof.

2. A compound according to Ia as defined in claim 1 having the following structural formulae (Ic and Id):

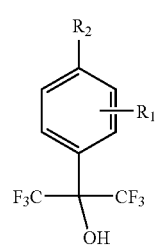

(Ic)

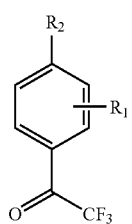

(Id)

wherein $R_1$ is hydrogen, halo, hydroxyl or cyano.

3. A compound according to Ic and Id as defined in claim 2 wherein $R_2$ is selected from the following formulae:

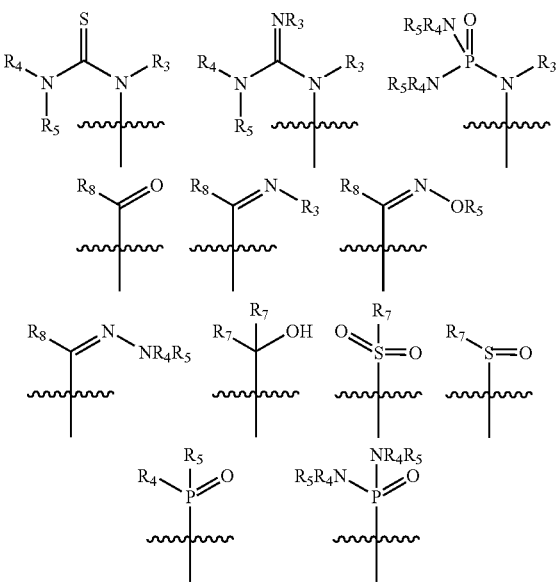

wherein $R_3$, $R_4$, $R_5$, $R_6$, $R_7$, and $R_8$ are defined as above.

4. A compound according to Ic and Id as defined in claim 2 wherein $R_2$ is selected from the following formulae:

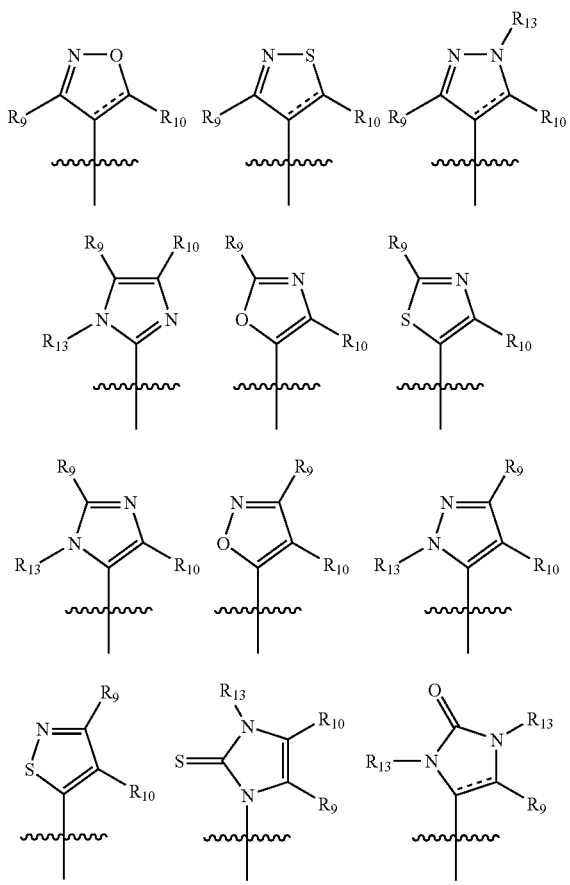

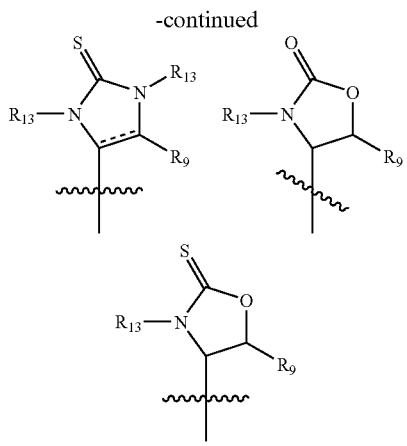

wherein $R_9$, $R_{10}$, and $R_{13}$ are defined as above.

5. A compound according to claim 1 selected from the group consisting of:
3-{4-[2,2,2-Trifluoro-1-hydroxy-1-(trifluoromethyl) ethyl]phenyl}-4,5-dihydroisoxazole-5-carboxylic acid;
5-amino-3-{4-[2,2,2-trifluoro-1-hydroxy-1-(trifluoromethyl)ethyl]phenyl}isoxazole-4-carbonitrile;
Ethyl 5-pyridin-3-yl-3-{4-[2,2,2-trifluoro-1-hydroxy-1-(trifluoromethyl)ethyl]phenyl}isoxazole-4-carboxylate;
Methyl 5-[(methyloxy)methyl]-3-{4-[2,2,2-trifluoro-1-hydroxy-1-(trifluoromethyl)ethyl]phenyl}isoxazole-4-carboxylate;
Methyl 3-{4-[2,2,2-trifluoro-1-hydroxy-1-(trifluoromethyl)ethyl]phenyl}-4,5-dihydroisoxazole-5-carboxylate;
Diethyl 4-[2,2,2-trifluoro-1-hydroxy-1-(trifluoromethyl) ethyl]phenyl amidophosphate;
Diethyl ethyl{4-[2,2,2-trifluoro-1-hydroxy-1-(trifluoromethyl)ethyl]phenyl}amidophosphate;
Diethyl 4-[2,2,2-trifluoro-1-hydroxy-1-(trifluoromethyl) ethyl]phenyl phosphonate; and
Phenyl{4-[2,2,2-trifluoro-1-hydroxy-1-(trifluoromethyl) ethyl]phenyl}phosphinic acid.

6. The compound of claim 1, wherein the compound has formula (Ia).

7. The compound of claim 6, wherein $R_2$ is $NR_3C(S)NR_4R_5$ or $NR_3C(=NR_3)NR_4R_5$.

8. The compound of claim 7, wherein $R_4$ and $R_5$, and the N atom to which they are attached form a 5-7 membered ring.

9. The compound of claim 8, wherein $R_4$ and $R_5$, and the N atom to which they are attached form a morpholine ring.

10. The compound of claim 9, wherein X is $CF_3$, A is O, Y is H, and Z is F.

11. The compound of claim 1, wherein $R_2$ is $NR_3C(S)NR_4R_5$ or $NR_3C(=NR_3)NR_4R_5$.

12. The compound of claim 1, wherein X is $CF_3$, A is O, Y is H, and Z is F.

13. The compound of claim 3, wherein the compound is selected from the group consisting of:
N-(4-Cyanobutyl)-N-{4-[2,2,2-trifluoro-1-hydroxy-1(trifluoromethyl)ethyl]phenyl}morpholine-4-carbothioamide;
Methyl 5-((morpholin4-ylcarbonothioyl){4-[2,2,2-trifluoro-1-hydroxy-1-(trifluoromethyl)ethyl]phenyl}amino)pentanoate;
[Bis(1-methylethyl)amino](butyl{4-[2,2,2-trifluoro-1-hydroxy-1-(trifluoromethyl)ethyl]phenyl}amino)methaniminium chloride;
(Butyl{4-[2,2,2-trifluoro-1-hydroxy-1-(trifluoromethyl) ethyl]phenyl}amino)(pyrrolidin-1-yl)methaniminium chloride;
(Butyl{4-[2,2,2-trifluoro-1-hydroxy-1-(trifluoromethyl) ethyl]phenyl}amino)(diethylamino)methaniminium chloride;
N-[4-(3-Methyl-1,2,4-oxadiazol-5-yl)butyl]-N-{4-[2,2,2-trifluoro-1-hydroxy-1-(trifluoromethyl)ethyl] phenyl}morpholine-4-carbothioamide;
(Butyl{4-[2,2,2-trifluoro-1-hydroxy-1-(trifluoromethyl) ethyl]phenyl}amino)(piperidin-1-yl)methaniminium chloride;
N-[(4-Cyanophenyl)methyl]-N-{4-[2,2,2-trifluoro-1-hydroxy-1-(trifluoromethyl)ethyl]phenyl}morpholine-4-carbothioamide;
N-{4-[2,2,2-Trifluoro-1-hydroxy-1-(trifluoromethyl) ethyl]phenyl}-N-{[4-(trifluoromethyl)phenyl] methyl}morpholine-4-carbothioamide;
N-[3-(1H-pyrrol-1-yl)propyl]-N-{4-[2,2,2-trifluoro-1-hydroxy-1-(trifluoromethyl)ethyl]phenyl}morpholine-4-carbothioamide;
N-Butyl-N',N'-diethyl-N-{4-[2,2,2-trifluoro-1-hydroxy-1-(trifluoromethyl)ethyl]phenyl}thiourea;
(Dimethylamino)(propyl{4-[2,2,2-trifluoro-1-hydroxy-1-(trifluoromethyl)ethyl]phenyl}amino)methaniminium chloride;
(Butyl{4-[2,2,2-trifluoro-1-hydroxy-1-(trifluoromethyl) ethyl]phenyl}amino)(morpholin-4-yl)methaniminium chloride;
(Butyl{4-[2,2,2-trifluoro-1-hydroxy-1-(trifluoromethyl) ethyl]phenyl}amino)(dibutylamino)methaniminium chloride;
[Bis(1-methylethyl)amino]({4-[2,2,2-trifluoro-1-hydroxy-1-(trifluoromethyl)ethyl]phenyl}amino)methaniminium chloride;
N-Ethyl-N-{4-[2,2,2-trifluoro-1-hydroxy-1-(trifluoromethyl)ethyl]phenyl}morpholine-4-carbothioamide;
N,N,1-Trimethyl-3-{4-[2,2,2-trifluoro-1-hydroxy-1-(trifluoromethyl)ethyl]phenyl}-4,5-dihydro-1H-pyrazole-5-carboxamide;
1,1-Dimethylethyl3-{[(3-{4-[2,2,2-trifluoro-1-hydroxy-1-(trifluoromethyl)ethyl]phenyl}-4,5-dihydroisoxazol-5-yl)carbonyl]amino}propanoate;
(1Z)-1-{4-[2,2,2-Trifluoro-1-hydroxy-1-(trifluoromethyl) ethyl]phenyl}butan-1-one O-(2-morpholin4-yl-2-oxoethyl)oxime;
(Z)-Phenyl{4-[2,2,2-trifluoro-1-hydroxy-1-(trifluoromethyl)ethyl]phenyl}methanone O-methyloxime;
(1Z)-1-{4-[2,2,2-Trifluoro-1-hydroxy-1-(trifluoromethyl) ethyl]phenyl}pentan-1-one O-methyloxime;
3-Methyl-1-{4-[2,2,2-trifluoro-1-hydroxy-1-(trifluoromethyl)ethyl]phenyl}butan-1-one;
1-{4-[2,2,2-Trifluoro-1-hydroxy-1-(trifluoromethyl) ethyl]phenyl}pentan-1-one;
2-Methyl-1-{4-[2,2,2-trifluoro-1-hydroxy-1-(trifluoromethyl)ethyl]phenyl}propan-1-one;
1-{4-[2,2,2-Trifluoro-1-hydroxy-1-(trifluoromethyl) ethyl]phenyl}butan-1-one;
(1E)-1-{4-[2,2,2-Trifluoro-1-hydroxy-1-(trifluoromethyl) ethyl]phenyl}butan-1-one O-methyloxime;
(1Z)-1-{4-[2,2,2-Trifluoro-1-hydroxy-1-(trifluoromethyl) ethyl]phenyl}butan-1-one O-ethyloxime;
(1Z)-1-{4-[2,2,2-Trifluoro-1-hydroxy-1-(trifluoromethyl) ethyl]phenyl}butan-1-one oxime;

(1Z)-1-{4-[2,2,2-Trifluoro-1-hydroxy-1-(trifluoromethyl)ethyl]phenyl}butan-1-one O-(1-methylethyl)oxime;
Phenyl{4-[2,2,2-trifluoro-1-hydroxy-1-(trifluoromethyl)ethyl]phenyl}methanone;
(1Z)-1-{4-[2,2,2-Trifluoro-1-hydroxy-1-(trifluoromethyl)ethyl]phenyl}butan-1-one O-[2-(phenyloxy)ethyl]oxime;
(1Z)-1-{4-[2,2,2-Trifluoro-1-hydroxy-1-(trifluoromethyl)ethyl]phenyl}butan-1-one O-(phenylmethyl)oxime; and
(1Z)-1-{4-[2,2,2-Trifluoro-1-hydroxy-1-(trifluoromethyl)ethyl]phenyl)butan-1-one O-(2-methylpropyl)oxime.

14. The compound of claim 4, wherein the compound is selected from the group consisting of:

1-Methyl-3-{4-[2,2,2-trifluoro-1-hydroxy-1-(trifluoromethyl)ethyl]phenyl}-1H-pyrazole-4-carbonitrile;
1-(1-Phenyl-3-{4-[2,2,2-trifluoro-1-hydroxy-1-(trifluoromethyl)ethyl]phenyl}-1H-pyrazol-4-yl)ethanone;
Methyl 5-amino-1-phenyl-3-{4-[2,2,2-trifluoro-1-hydroxy-1-(trifluoromethyl)ethyl]phenyl}-1H-pyrazole-4-carboxylate;
1,1,1,3,3,3-Hexafluoro-2-[4-(4-phenyl-1-propyl-1H-imidazol-2-yl)phenyl]propan-2-ol;
1,1,1,3,3,3-Hexafluoro-2-{4-[4-(hydroxymethyl)-1H-imidazol-2-yl]phenyl}propan-2-ol;
1,1,1,3,3,3-Hexafluoro-2[4-(4-methyl-1H-imidazol-2-yl)phenyl]propan-2-ol;
(2-{4-[2,2,2-Trifluoro-1-hydroxy-1-(trifluoromethyl)ethyl]phenyl}-1H-imidazol-4-yl)methyl2-methylpropanoate; 1,1,1,3,3,3-Hexafluoro-2-[4-(1-propyl-4,5-dipyridin-3-yl-1H-imidazol-2-yl)phenyl]propan-2-ol;
1,1,1,3,3,3-Hexafluoro-2-[4-(4-pyridin-3-yl-1H-imidazol-2-yl)phenyl]propan-2-ol;
N-Butyl-4-phenyl-1-propyl-2-{4-[2,2,2-trifluoro-1-hydroxy-1-(trifluoromethyl)ethyl]phenyl}-1H-imidazole-5-carboxamide;
N-Butyl-4-phenyl-1-pyridin-3-ylmethyl)-2-{4-[2,2,2-trifluoro-1-hydroxy-1-(trifluoromethyl)ethyl]phenyl}-1H-imidazole-5-carboxamide;
N-Butyl-1-(2-morpholin-4-ylethyl)4-phenyl-2-{4-[2,2,2-trifluoro-1-hydroxy-1-(trifluoromethyl)ethyl]phenyl}-1H-imidazole-5-carboxamide;
N-Butyl-1-(2-cyanoethyl)-4-phenyl-2-{4-[2,2,2-trifluoro-1-hydroxy-1-(trifluoromethyl)ethyl]phenyl}-1H-imidazole-5-carboxamide;
N-Butyl-1-(3-hydroxypropyl)-4-phenyl-2-{4-[2,2,2-trifluoro-1-hydroxy-1-(trifluoromethyl)ethyl]phenyl}-1H-imidazole-5-carboxamide;
2-[4-(4,5-Diphenyl-1-propyl-1H-imidazol-2-yl)phenyl]-1,1,1,3,3,3-hexafluoropropan-2-ol;
N-Butyl-1-(1-methylethyl)-4-phenyl-2-{4-[2,2,2-trifluoro-1-hydroxy-1-(trifluoromethyl)ethyl]phenyl}-1H-imidazole-5-carboxamide;
Methyl{[(4-phenyl-1-propyl-2-{4-[2,2,2-trifluoro-1-hydroxy-1-(trifluoromethyl)ethyl]phenyl}-1H-imidazol-5-yl)carbonyl]amino}acetate;
{[(4-Phenyl-1-propyl-2-{4-[2,2,2-trifluoro-1-hydroxy-1-(trifluoromethyl)ethyl]phenyl}-1H-imidazol-5-yl)carbonyl]amino}acetic acid;
N-Butyl-1-(2-methylpropyl)-4-phenyl-2-{4-[2,2,2-trifluoro-1-hydroxy-1-(trifluoromethyl)ethyl]phenyl}-1H-imidazole-5-carboxamide;
N-Butyl-1-propyl-pyridin-3-yl-2-{4-[2,2,2-trifluoro-1-hydroxy-1-(trifluoromethyl)ethyl]phenyl}-1H-imidazole-5-carboxamide;
N-[(2-{4-[2,2,2-Trifluoro-1-hydroxy-1-(trifluoromethyl)ethyl]phenyl}-1H-imidazol-4-yl)methyl]methanesulfonamide;
N-Butyl-4-(4-cyanophenyl)-1-propyl-2-{4-[2,2,2-trifluoro-1-hydroxy-1-(trifluoromethyl)ethyl]phenyl}-1H-imidazole-5-carboxamide;
2-[4-(5-Amino-3-phenyl-1H-pyrazol-4-yl)phenyl]-1,1,1,3,3,3-hexafluoropropan-2-ol;
2-{4-[5-Amino-1-(1,1-dimethylethyl)-3-methyl-1H-pyrazol-4-yl]phenyl}-1,1,1,3,3,3-hexafluoropropan-2-ol;
4-(5-Amino-3-methyl-4-{4-[2,2,2-trifluoro-1-hydroxy-1-(trifluoromethyl)ethyl]phenyl}-1H-pyrazol-1-yl)benzonitrile;
Ethyl (5-amino-3-methyl-4-{4-[2,2,2-trifluoro-1-hydroxy-1-(trifluoromethyl)ethyl]phenyl}-1H-pyrazol-1-yl)acetate;
N-(3-(1-Methylethyl)-4-{4-[2,2,2-trifluoro-1-hydroxy-1-(trifluoromethyl)ethyl]phenyl}isoxazol-5-yl)pent-4-enamide;
2-[4-(5-Amino-3-pyridin-4-ylisoxazol-4-yl)phenyl]-1,1,1,3,3,3-hexafluoropropan-2-ol;
2-Methyl-N-(3-pyridin-4-yl-4-{4-[2,2,2-trifluoro-1-hydroxy-1-(trifluoromethyl)ethyl]phenyl}isoxazol-5-yl)propanamide;
(2E)-3-(5-Methyl-4-{4-[2,2,2-trifluoro-1-hydroxy-1-(trifluoromethyl)ethyl]phenyl}isoxazol-3-yl)prop-2-enenitrile;
N-(3-(1-Methylethyl)-4-{4-[2,2,2-trifluoro-1-hydroxy-1-(trifluoromethyl)ethyl]phenyl}isoxazol-5-yl)pyridine-4-carboxamide;
N-(5-methyl-4-{4-[2,2,2-trifluoro-1-hydroxy-1-(trifluoromethyl)ethyl]phenyl}isoxazol-3-yl)pyridine-4-carboxamide;
4-Cyano-N-(3-(1-methylethyl)-4-{4-[2,2,2-trifluoro-1-hydroxy-1-(trifluoromethyl)ethyl]phenyl}isoxazol-5-yl)benzamide;
2-[4-(3,5-Dimethylisoxazol-4-yl)phenyl]-1,1,1,3,3,3-hexafluoropropan-2-ol;
N-(3-(1-Methylethyl)-4-{4-[2,2,2-trifluoro-1-hydroxy-1-(trifluoromethyl)ethyl]phenyl}isoxazol-5-yl)-2-phenylbutanamide;
2-{4-[5-Amino-3-(1-methylethyl)isoxazol-4-yl]phenyl}-1,1,1,3,3,3-hexafluoropropan-2-ol;
N-(3,5-Dimethylisoxazol-4-yl)-N'-(5-methyl-4-{4-[2,2,2-trifluoro-1-hydroxy-1-(trifluoromethyl)ethyl]phenyl}isoxazol-3-yl)urea;
2-(4-{5-Amino-3-[(ethyloxy)methyl]isoxazol-4-yl}phenyl)-1,1,1,3,3,3-hexafluoropropan-2-ol;
3-(5-Amino-4-{4-[2,2,2-trifluoro-1-hydroxy-1-(trifluoromethyl)ethyl]phenyl}isoxazol-3-yl)propan-1-ol;
2-[4-(5-Amino-3-butylisoxazol-4-yl)phenyl]-1,1,1,3,3,3-hexafluoropropan-2-ol;
2-[4-(5-Amino-3-ethylisoxazol-4-yl)phenyl]-1,1,1,3,3,3-hexafluoropropan-2-ol;
N,5-Dimethyl-N-(methyloxy)-4-{4-[2,2,2-trifluoro-1-hydroxy-1-(trifluoromethyl)ethyl]phenyl}isoxazole-3-carboxamide;
2-Methyl-N-(3-phenyl-4-{4-[2,2,2-trifluoro-1-hydroxy-1-(trifluoromethyl)ethyl]phenyl}isoxazol-5-yl)propanamide;
1-(5-Methyl-4-{4-[2,2,2-trifluoro-1-hydroxy-1-(trifluoromethyl)ethyl]phenyl}isoxazol-3-yl)butan-1-one;
Ethyl 5-methyl-4-{4-[2,2,2-trifluoro-1-hydroxy-1-(trifluoromethyl)ethyl]phenyl}isoxazole-3-carboxylate;
2-Methyl-N-(5-methyl-4-{4-[2,2,2-trifluoro-1-hydroxy-1-(trifluoromethyl)ethyl]phenyl}isoxazol-3-yl)propanamide;

N,N,5-Trimethyl-4-{4-[2,2,2-trifluoro-1-hydroxy-1-(trifluoromethyl)ethyl]phenyl}isoxazole-3-carboxamide;

4-[(3-(1-Methylethyl)-4-{4-[2,2,2-trifluoro-1-hydroxy-1-(trifluoromethyl) ethyl]phenyl}isoxazol-5-yl)amino]-4-oxo-2-phenylbutanoic acid;

1,1,1,3,3,3-Hexafluoro-2-{4-[3-(hydroxymethyl)-5-methylisoxazol-4-yl]phenyl}propan-2-ol;

1,1-Dimethylethyl 5-methyl-4-{4-[2,2,2-trifluoro-1-hydroxy-1-(trifluoromethyl)ethyl]phenyl}isoxazol-3-yl-carbamate;

2-(4-{5-Amino-3-[(2E)-but-2-enyl]isoxazol-4-yl}phenyl)-1,1,1,3,3,3-hexafluoropropan-2-ol;

3-(5-Amino-4-{4-[2,2,2-trifluoro-1-hydroxy-1-(trifluoromethyl)ethyl]phenyl}isoxazol-3-yl)propanoic acid;

4-(5-Amino-4-{4-[2,2,2-trifluoro-1-hydroxy-1-(trifluoromethyl)ethyl]phenyl}isoxazol-3-yl)phenol;

Ethyl 4-(methylthio)-2-({[(5-methyl-4-{4-[2,2,2-trifluoro-1-hydroxy-1-(trifluoromethyl)ethyl]phenyl}isoxazol-3-yl)amino]carbonyl}amino)butanoate;

N-(5-Methyl-4-{4-[2,2,2-trifluoro-1-hydroxy-1-(trifluoromethyl)ethyl]phenyl}isoxazol-3-yl)hexanamide;

Ethyl 4-methyl-2-({[(5-methyl-4-{4-[2,2,2-trifluoro-1-hydroxy-1-(trifluoromethyl)ethyl]phenyl}isoxazol-3-yl)amino]carbonyl}anlino)pentanoate;

({[(5-Methyl-4-{4-[2,2,2-trifluoro-1-hydroxy-1-(trifluoromethyl)ethyl]phenyl}isoxazol-3-yl)amino]carbonyl}amino)acetic acid;

N-(5-Methyl-4-{4-[2,2,2-trifluoro-1-hydroxy-1-(trifluoromethyl)ethyl]phenyl}isoxazol-3-yl)-N'-phenylurea;

2-[4-(5-Amino-3-furan-3-ylisoxazol-4-yl)phenyl]-1,1,1,3,3,3-hexafluoropropan-2-ol;

5-Methyl-4-{4-[2,2,2-trifluoro-1-hydroxy-1-(trifluoromethyl)ethyl]phenyl}isoxazole-3-carboxylic acid;

N-(5-Methyl-4-{4-[2,2,2-trifluoro-1-hydroxy-1-(trifluoromethyl)ethyl]phenyl}isoxazol-3-yl)acetamide;

4-(Methylthio)-2-({[(5-methyl-4-{4-[2,2,2-trifluoro-1-hydroxy-1-(trifluoromethyl)ethyl]phenyl}isoxazol-3-yl)amino]carbonyl}amino)butanoic acid;

2-{4-[5-Amino-3-(1H-indol-3-ylmethyl)isoxazol-4-yl]phenyl}-1,1,1,3,3,3-hexafluoropropan-2-ol;

2-[4-(5-Amino-3-phenylisoxazol-4-yl)phenyl]-1,1,1,3,3,3-hexafluoropropan-2-ol;

N-(5-Methyl-4-{4-[2,2,2-trifluoro-1-hydroxy-1-(trifluoromethyl)ethyl]phenyl}isoxazol-3-yl)-3-phenylpropanamide;

2-(4-{5-Amino-3-[4-(methyloxy)phenyl]isoxazol-4-yl}phenyl)-1,1,1,3,3,3-hexafluoropropan-2-ol;

N-(5-Methyl-4-{4-[2,2,2-trifluoro-1-hydroxy-1-(trifluoromethyl)ethyl]phenyl}isoxazol-3-yl)-N'-(2-phenylethyl)urea;

Ethyl (2E)-3-(5-methyl-4-{4-[2,2,2-trifluoro-1-hydroxy-1-(trifluoromethyl)ethyl]phenyl}isoxazol-3-yl)prop-2-enoate;

2-{4-[5-Amino-3-(trifluoromethyl)isoxazol-4-yl]phenyl}-1,1,1,3,3,3-hexafluoropropan-2-ol;

4-Methyl-2-({[(5-methyl-4-{4-[2,2,2-trifluoro-1-hydroxy-1-(trifluoromethyl)ethyl]phenyl}isoxazol-3-yl)amino]carbonyl}amino)pentanoic acid;

Ethyl ({[(5-methyl-4-{4-[2,2,2-trifluoro-1-hydroxy-1-(trifluoromethyl)ethyl]phenyl}isoxazol-3-yl)amino]carbonyl}amino)acetate;

N-(1-Methylethyl)-N'-(3-phenyl-4-{4-[2,2,2-trifluoro-1-hydroxy-1-(trifluoromethyl)ethyl]phenyl}isoxazol-5-yl)urea;

Bis(1,1-dimethylethyl)5-methyl-4-{4-[2,2,2-trifluoro-1-hydroxy-1-(trifluoromethyl)ethyl]phenyl}isoxazol-3-ylimidodicarbonate;

N-Cyclohexyl-N'-(5-methyl-4-{4-[2,2,2-trifluoro-1-hydroxy-1-(trifluoromethyl)ethyl]phenyl}isoxazol-3-yl)urea;

2-{4-[5-Amino-3-(phenylmethyl)isoxazol-4-yl]phenyl}-1,1,1,3,3,3-hexafluoropropan-2-ol; and 5-Methyl-4-{4-[2,2,2-trifluoro-1-hydroxy-1-(trifluoromethyl)ethyl]phenyl}isoxazol-3-aminium trifluoroacetate.

\* \* \* \* \*